US009877929B2

(12) United States Patent
McHale et al.

(10) Patent No.: US 9,877,929 B2
(45) Date of Patent: *Jan. 30, 2018

(54) TOPICAL VITAMIN D AND UBIQUINOL ORAL SUPPLEMENT COMPOSITIONS

(71) Applicant: Premier Dental Products Company, Plymouth Meeting, PA (US)

(72) Inventors: William A. McHale, Collegeville, PA (US); Dale G. Brown, Wharton, TX (US)

(73) Assignee: Premier Dental Products Company, Plymouth Meeting, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/650,991

(22) Filed: Oct. 12, 2012

(65) Prior Publication Data

US 2013/0095155 A1  Apr. 18, 2013

Related U.S. Application Data

(60) Provisional application No. 61/546,811, filed on Oct. 13, 2011.

(51) Int. Cl.
| | | |
|---|---|---|
| *A61K 31/09* | (2006.01) | |
| *A61K 31/122* | (2006.01) | |
| *A61K 47/10* | (2017.01) | |
| *A61K 9/00* | (2006.01) | |
| *A61K 47/24* | (2006.01) | |
| *A61K 47/26* | (2006.01) | |
| *A61K 9/06* | (2006.01) | |
| *A61K 31/593* | (2006.01) | |
| *A61C 15/04* | (2006.01) | |
| *A61C 19/06* | (2006.01) | |
| *A61K 8/34* | (2006.01) | |
| *A61K 8/67* | (2006.01) | |
| *A61Q 11/00* | (2006.01) | |
| *A61K 8/891* | (2006.01) | |
| *A61K 8/90* | (2006.01) | |

(52) U.S. Cl.
CPC ............ *A61K 31/09* (2013.01); *A61C 15/041* (2013.01); *A61C 19/063* (2013.01); *A61K 8/345* (2013.01); *A61K 8/67* (2013.01); *A61K 8/891* (2013.01); *A61K 8/90* (2013.01); *A61K 9/006* (2013.01); *A61K 9/0063* (2013.01); *A61K 9/06* (2013.01); *A61K 31/122* (2013.01); *A61K 31/593* (2013.01); *A61K 47/10* (2013.01); *A61K 47/24* (2013.01); *A61K 47/26* (2013.01); *A61Q 11/00* (2013.01)

(58) Field of Classification Search
USPC ........................................................ 514/167
See application file for complete search history.

(56) References Cited

U.S. PATENT DOCUMENTS

| 3,442,842 | A | 5/1969 | Bonin |
|---|---|---|---|
| 4,259,316 | A | 3/1981 | Nakashima et al. |
| 4,296,096 | A | 10/1981 | Pierce |
| 4,647,451 | A | 3/1987 | Piechota |
| 4,652,441 | A | 3/1987 | Okada et al. |
| 4,711,782 | A | 12/1987 | Okada et al. |
| 4,911,927 | A | 3/1990 | Hill et al. |
| 4,942,034 | A | 7/1990 | Hill et al. |
| 5,009,881 | A | 4/1991 | Hill et al. |
| 5,032,387 | A | 7/1991 | Hill et al. |
| 5,037,639 | A | 8/1991 | Tung |
| 5,057,306 | A | 10/1991 | Hill et al. |
| 5,057,307 | A | 10/1991 | Hill et al. |
| 5,057,309 | A | 10/1991 | Hill et al. |
| 5,098,711 | A | 3/1992 | Hill et al. |
| 5,165,913 | A | 11/1992 | Hill et al. |
| 5,268,167 | A | 12/1993 | Tung |
| 5,427,768 | A | 6/1995 | Tung |
| 5,437,857 | A | 8/1995 | Tung |
| 5,460,803 | A | 10/1995 | Tung |
| 5,538,667 | A | 7/1996 | Hill et al. |

(Continued)

FOREIGN PATENT DOCUMENTS

| CN | 1093058 A | 10/1994 |
|---|---|---|
| CN | 1190342 A | 8/1998 |

(Continued)

OTHER PUBLICATIONS

Barry, Robert: "The Power of Ubiquinol" The Key to Energy, Vitality, and a Healthy Heart. 2010. (5 pages).
Tang, et al.: "HPLC Analysis of Reduced and Oxidized Coenzyme $Q_{10}$ in Human Plasma", Clinical Chemistry 47:2, pp. 256-265, 2001.
Jacob M. ten Cate: "Current Concepts on the Theories of the Mechanism of Action of Fluoride", Academic Centre for Dentistry Amsterdam (ACTA), Department of Cariology Endodontology Pedodontology, Amsterdam the Netherlands, pp. 325-329, 1999.
Tung, Ming S.: "CE2, Amorphous Calcium Phosphates for Tooth Mineralization", Sep. 2004, vol. 25, No. 9, American Dental Association Foundation.
Charig, Andrew: "CE 3, Enamel Mineralization by Calcium-Containing Bicarbonete Toothpastes: Assessment by Various Techniques", Compendium, Sep. 2004, vol. 25, No. 9.

(Continued)

*Primary Examiner* — Bethany P Barham
*Assistant Examiner* — Dominic Lazaro
(74) *Attorney, Agent, or Firm* — Cozen O'Connor

(57) ABSTRACT

A topical vitamin D and UBIQUINOL supplement composition useful in treating oral inflammation and reducing oxidative stress comprising: a supplement mixture of vitamin D and UBIQUINOL in an aqueous-free emulsion containing: spilanthes extract, stabilizing compositions for UBIQUINOL and trans-oral mucosal absorption facilitators for the supplement mixture; where the emulsion forms a mucoadhesive gel in the presence of saliva, that effects passive diffusion through the oral mucosa of the supplement mixture and spilanthes extract regulating: in vivo availability and immune response of the supplement mixture, and maintaining adequate levels of circulating vitamin D and of adjunctively administered UBIQUINOL, while minimizing the risk of hypercalcemia.

19 Claims, No Drawings

(56) References Cited

U.S. PATENT DOCUMENTS

| | | | |
|---|---|---|---|
| 5,562,895 A | 10/1996 | Tung | |
| 5,614,175 A | 3/1997 | Winston et al. | |
| 5,645,841 A | 7/1997 | Hill et al. | |
| 5,651,959 A | 7/1997 | Hill et al. | |
| 5,665,374 A | 9/1997 | Hill et al. | |
| 5,665,382 A | 9/1997 | Grinstaff et al. | |
| 5,711,935 A | 1/1998 | Hill et al. | |
| 5,925,595 A | 7/1999 | Seitz et al. | |
| 5,952,317 A | 9/1999 | Deluca et al. | |
| 6,054,119 A | 4/2000 | Hurme et al. | |
| 6,086,373 A | 7/2000 | Schiff et al. | |
| 6,159,449 A | 12/2000 | Winston et al. | |
| 6,184,255 B1 | 2/2001 | Tatsumasa et al. | |
| 6,441,050 B1* | 8/2002 | Chopra | 514/675 |
| 6,534,091 B1 | 3/2003 | Garces Garces et al. | |
| 6,545,077 B2 | 4/2003 | Hill et al. | |
| 6,569,408 B1 | 5/2003 | Yue et al. | |
| 6,575,176 B1 | 6/2003 | Hill et al. | |
| 6,740,338 B1* | 5/2004 | Chopra | 424/456 |
| 7,017,591 B2 | 3/2006 | Brown et al. | |
| 7,025,986 B2 | 4/2006 | Brown et al. | |
| 7,152,611 B2 | 12/2006 | Brown et al. | |
| 7,303,921 B2 | 12/2007 | Littarru et al. | |
| 7,897,169 B2 | 3/2011 | Ueda et al. | |
| 2002/0090398 A1 | 7/2002 | Dunn et al. | |
| 2003/0165442 A1 | 9/2003 | Baig et al. | |
| 2003/0198604 A1 | 10/2003 | Lawlor | |
| 2004/0057908 A1 | 3/2004 | Bowen | |
| 2004/0126335 A1 | 7/2004 | Faller et al. | |
| 2004/0258634 A1* | 12/2004 | Cazor et al. | 424/52 |
| 2005/0196440 A1 | 9/2005 | Masters et al. | |
| 2006/0093558 A1* | 5/2006 | Lin et al. | 424/47 |
| 2006/0120980 A1 | 6/2006 | Eberl | |
| 2006/0177384 A1* | 8/2006 | Brown | 424/49 |
| 2006/0286046 A1 | 12/2006 | Haber | |
| 2007/0025928 A1 | 2/2007 | Glandorf et al. | |
| 2007/0190090 A1* | 8/2007 | Brown | 424/401 |
| 2008/0039434 A1 | 2/2008 | Colli | |
| 2008/0044454 A1 | 2/2008 | Yang et al. | |
| 2008/0050408 A1 | 2/2008 | Hayman et al. | |
| 2008/0069781 A1 | 3/2008 | Neuberger | |
| 2008/0095719 A1* | 4/2008 | Herrmann et al. | 424/48 |
| 2008/0152598 A1 | 6/2008 | Basic | |
| 2008/0152599 A1 | 6/2008 | Brignoli et al. | |
| 2008/0175918 A1 | 7/2008 | Laulicht | |
| 2008/0226710 A1* | 9/2008 | Fantuzzi | 424/456 |
| 2008/0247973 A1 | 10/2008 | Baig et al. | |
| 2008/0286214 A1 | 11/2008 | Brown et al. | |
| 2008/0295960 A1 | 12/2008 | Schalau, II et al. | |
| 2009/0042161 A1 | 2/2009 | Jodaikin et al. | |
| 2009/0087501 A1 | 4/2009 | Cummins | |
| 2009/0188520 A1 | 7/2009 | Brown | |
| 2009/0232752 A1* | 9/2009 | Carson et al. | 424/59 |
| 2009/0280078 A1 | 11/2009 | Belfer | |
| 2010/0135918 A1 | 6/2010 | Kim et al. | |
| 2010/0330003 A1 | 12/2010 | Robinson et al. | |
| 2011/0014136 A1 | 1/2011 | Kohli et al. | |
| 2011/0104052 A1 | 5/2011 | Barnett et al. | |
| 2011/0118217 A1 | 5/2011 | Gudmundsson et al. | |
| 2012/0021031 A1 | 1/2012 | Chopra et al. | |
| 2012/0064136 A1 | 3/2012 | Baker et al. | |
| 2012/0129135 A1 | 5/2012 | Yang et al. | |
| 2012/0171128 A1 | 7/2012 | Ramirez | |
| 2012/0207686 A1 | 8/2012 | Fruge et al. | |
| 2012/0245080 A1 | 9/2012 | Goolsbee et al. | |
| 2013/0344120 A1 | 12/2013 | Scott et al. | |

FOREIGN PATENT DOCUMENTS

| | | |
|---|---|---|
| CN | 101056606 A | 10/2007 |
| EP | 0559262 A1 | 9/1993 |
| EP | 0868903 A2 | 10/1998 |
| JP | H11506769 A | 6/1999 |
| JP | H11243910 A | 9/1999 |
| JP | 2004535453 A | 11/2004 |
| JP | 2008534629 A | 8/2008 |
| WO | 1995011746 A1 | 5/1995 |
| WO | 1996039116 A | 12/1996 |
| WO | 1996039116 A1 | 12/1996 |
| WO | WO 9639116 A1 * | 12/1996 |
| WO | 2001026577 A1 | 4/2001 |
| WO | 2001068046 A2 | 9/2001 |
| WO | 2003068173 A1 | 8/2003 |
| WO | 2006105615 A1 | 10/2006 |
| WO | WO 2007/036802 | 4/2007 |
| WO | 2007092811 A1 | 8/2007 |
| WO | WO 2007099398 A2 * | 9/2007 |
| WO | 2008041055 A1 | 4/2008 |
| WO | 2008047882 A1 | 4/2008 |
| WO | 2009080022 A1 | 7/2009 |
| WO | 2009153634 A | 12/2009 |
| WO | 2010010394 A2 | 1/2010 |
| WO | 2013039906 A1 | 3/2013 |
| WO | 2013095366 A1 | 6/2013 |
| WO | 2014001132 A1 | 1/2014 |

OTHER PUBLICATIONS

Litkowski, Leonard J.: "CE4, Intraoral Evaluation of Mineralization of Cosmetic Defects by a Toothpaste Containing Calcium, Fluoride, and Sodium Bicarbonate," Compendium, Sep. 2004, vol. 25, No. 9.

Schemehorn, B.R.: "Remineralization by Fluoride Enhanced with Calcium and Phosphate Ingredients", Indiana University School of Dentistry, The British Library, Enamelon, Inc. Cranbury, NJ.

Xu, HHK: "Strong Nanocomposites with Ca PO4, and F Release for Caries Inhibition", Critical Reviews in Oral Biology & Medicine, Jan. 2009.

Roveri, Norberto: "Surface Enamel Remineralization: Biomimetic Apatite Nanocrystals and Fluoride Ions Different Effects", vol. 2009, Article ID 746383, Journal Nanomaterials.

Thies, Curt: "A Survey of Microencapsulation Processes", Washington University, St. Louis, MO.

Lei, Y.: In Vitro Degradation of Novel Bioactive Polycaprolactone-20% Tricalcium Phosphate Composite Scaffolds for Bone Engineering, Materials and Science and Engineering, vol. 27, Issue 2, Mar. 2007.

Lowenstein, et al.: "Vaterite: A Mineralization Product of the hard Tissues of a Marine Organism (*Ascidiacea*)", Science, vol. 188, 1972, pp. 363-365.

Dimeloe et al. "Regulatory T cells, inflammation and the allergic response The role of glucocorticoids and Vitamin D", Journal of Steroid Biochemistry & Molecular Biology, vol. 120, 2010, 86-95.

McMahon et al. "Vitamin D-Mediated Induction of Innate Immunity in Gingival Epithelial Cellis", Infection and Immunity, vol. 79, 2011, p. 2250-2256.

International Search Report and Written Opinion dated Oct. 12, 2012 issued in corresponding International Patent Application No. PCT/US2013/064358.

Hewison, M., "Review: Vitamin D and the intracrinology of innate immunity", Molecular and Cellular Endocrinology, vol. 321, No. 2, pp. 103-111, 2010.

Holick, M.F., "Vitamin D Deficiency", New England Journal of Medicine, vol. 357, pp. 266-281, 2007.

Holick, M.F., "Vitamin D Status: Measurement, Interpretation, and Clinical Application", Annals of Epidemiology, vol. 19, No. 2, pp. 73-78, 2009.

Hong, Y.C., "Enhanced fluoride uptake from mouthrinses", J Dent Res., vol. 64, pp. 82-84, 1985.

International Search Report and Written Opinion dated Apr. 21, 2014 which issued in International Patent Application No. PCT/US2013/064504.

International Search Report and Written Opinion dated Jul. 2, 2015 which issued in International Patent Application No. PCT/US2015/025375.

International Search Report and Written Opinion dated Jul. 10, 2015 which issued in International Patent Application No. PCT/US2015/025385.

(56) References Cited

OTHER PUBLICATIONS

International Search Report and Written Opinion dated Jul. 2, 2015 which issued in International Patent Application No. PCT/US2015/025391.
International Search Report and Written Opinion dated Jul. 2, 2015 which issued in International Patent Application No. PCT/US2015/025396.
Kamen, D.L., et al., "Vitamin D and molecular actions on the immune system: modulation of innate and autoimmunity", J. Mol. Med., vol. 88, pp. 441-450, 2010.
Koch, G., "Effect of 250 and 1000 ppm fluoride dentifrice on caries; a three-year clinical study", Swed Dent J, vol. 6, pp. 233-238, 1982.
Littarru, G.P., et al., "Deficiency of coenzyme Q10 in gingival tissue from patients wit periodontal disease", Proc. Natl. Acad. Science USA, vol. 68, No. 10, pp. 2332-2335, Oct. 1971.
Margolis, H.C., et al., "Physicochemical perspectives on the cariostatic mechanisms of systemic and topical fluorides", J Dent Res, vol. 69 (Special Issue), pp. 606-613, 1990.
Marinho, V.C., et al., "Fluoride varnishes for preventing dental caries in children and adolescents (review)", Cochrane Database Syst Rev, vol. 3, CD002279, 2002.
McCree, J.T., et al., "Therapy with coenzyme Q10 for patients with periodontal disease. Effect of Coenzyme Q10 on Subgingival Microorganisms", Journal of Dental Health, vol. 43, No. 5, pp. 659-666, 1993.
Miley, D.D., et al., "Cross-sectional study of vitamin D and calcium supplementation effects on chronic periodontitis", J. Periodontol., vol. 80, No. 9, pp. 1433-1439, Sep. 2009.
Mitropoulos, C.M., et al., "Relative efficacy of dentifrices containing 250 or 1000 ppm F—in preventing dental caries—report of a 32-month clinical trial", Community Dent Health, vol. 1, pp. 193-200, 1984.
Mohammed, N.R., et al., "Effects of Fluoride on in vitro Enamel Demineralization Analyzed by 19F MAS-NMR", Caries Res, vol. 47, pp. 421-428, 2013.
Nizet, V., et al., "Cathelicidins and Innate Defense Against Invasive Bacterial Infection", Scandinavian Journal of Infectious Diseases, vol. 35, No. 9, pp. 670-676, 2003.
Øgaard, B., et al., "Relative cariostatic effects of KOH-soluble and KOH-insoluble fluoride in situ", J. Dent Res, vol. 69, pp. 1505-1507, 1990.
Øgaard, B., "CaF2 Formation: Cariostatic Properties and Factors of Enhancing the Effect", Caries Res., vol. 35 (Suppl 1), No. 11, pp. 40-44, 2001.
Oral Health: Different Ages/Different Stages: Birth to 12 12 Years, Ontario, Mar. 2009, pp. 1-24.
Park, K.S., et al., "The short vitamin D receptor is associated with increased risk for generalized aggressive periodontitis", Journal of Clinical Periodontology, vol. 33, No. 8, pp. 524-528, 2006.
Pendrys, D.G., "Risk of Enamel Fluorosis in Nonfluoridated and Optimally Fluoridated Populations: Considerations for the Dental Professional", Journal of the American Dental Association, vol. 131, No. 6, pp. 746-755, 2000.
Ripa, L.W., "A critique of topical fluoride methods (dentifrices, mouthrinses, operator-, and self-applied gels) in an era of decreased caries and increased fluorosis prevalence", J Public Health Dent., Winter, vol. 51, No. 1, pp. 23-41, 1991.
Rolla, G., et al., "Concentration of fluoride in plaque a possible mechanism", Scand. J. Dent. Res., vol. 85, pp. 149-151, 1977.
Rose, R.K., et al., "A quantitative study of calcium binding and aggregation in selected oral bacteria", J Dent Res, vol. 72, pp. 78-84, 1993.
Schaeken, M.J., et al., "Effects of fluoride and chlorhexidine on the microflora of dental root surfaces and the progression of root-surface caries", J Dent Res, vol. 70, No. 2, pp. 150-153, 1991.
Schmelzer, C., et al., "In vitro effects of the reduced form of coenzyme Q10 on secretion levels of TNF-α and chemokines in response to LPS in the human monocytic cell line THP-1," Journal of Clinical Biochemistry and Nutrition, vol. 44, No. 1, pp. 62-66, 2009.

Schreiber, C.T., et al., "Effects of rinses with an acidic calcium phosphate solution on fluoride uptake, caries and in situ plaque pH in rats", J Dent Res, vol. 67, pp. 959-963, 1988.
Stookey, G.K., "Critical evaluation of the composition and use of topical fluorides", J Dent Res, vol. 69 (Spec Iss), pp. 805-812, 1990.
Sun, J., "Vitamin D and mucosal immune function", Current Opinion in Gastroenterology,vol. 26, No. 6, pp. 591-594, Nov. 2010.
Tan, H.P., et al., "A randomized trial on root caries prevention in elders", J Dent Res, vol. 89, No. 10, pp. 1086-1090, 2010.
Ten Cate, J.M., "Review on Fluoride with special emphasis on calcium fluoride mechanisms in caries prevention", Eur. J. Oral Sci., vol. 105 (5 pt 2), pp. 461-465, Oct. 1997.
Tewari, A., et al., "Comparative evaluation of the role of NaF, APF, and Duraphat topical fluoride applications in the prevention of dental caries: a 2 1/2 year study", J Indian Soc Pedod Prev Dent, vol. 8, pp. 28-36, 1990.
Tung, M.S., et al., "Dental applications of amorphous calcium phosphates", J. Clin Dent, vol. 10, pp. 1-6, 1999.
Turner, D., et al., "The Interaction of Stannous Fluoride with Synthetic Hydroxyapatite: Modeling the Anticaries Effect", Ceramics—Silikaty, vol. 57, No. 1, pp. 1-6, 2013.
Vaikuntam, J., "Fluoride varnishes: should we be using them?", Pediatr Dent, vol. 22, pp. 513-516, 2000.
Vieth, R., et al., "Efficacy and safety of vitamin D3 intake exceeding the lowest observed adverse effect level", Am J Clin Nutr, vol. 73, No. 2, pp. 288-294, Feb. 2001.
Vogel, G.L., et al., "Salivary fluoride from fluoride dentifrices or rinses after use of a calcium pre-rinse or calcium dentifrice", Canes Res., vol. 40, pp. 449-454, 2006.
Vogel, G.L., et al., "Calcium Pre-Rinse Greatly Increases Overnight Salivary Fluoride after a 228 ppm Fluoride Rinse", Caries Res., vol. 42, No. 5, pp. 401-404, Sep. 2008.
Vogel, G.L., et al., "Ca Pre-Rinse Greatly Increases Plaque and Plaque F fluid F", J. Dent. Res., vol. 87, No. 5, pp. 466-469, May 2008.
Vogel, G.L., et al., "No Calcium-Fluoride-Like Deposits Detected in Plaque shortly after a Sodium Fluoride Mouthrinse", Caries Res., vol. 44, No. 2, pp. 108-115, 2010.
Walton, J.G., et al., "Textbook of Dental Pharmacology and Therapeutics", Oxford University Press 1994, pp. 149 and 154.
Wang, X.L., et al., "Cosupplementation with vitamin E and coenzyme Q10 reduces circulating markers of inflammation in baboons 1-3", Am. J. Clin. Nutr., vol. 80, No. 3, pp. 649-655, Sep. 2004.
Wang, C., et al., "Association Between Vitamin D Receptor Gene Polymorphisms and Severe Chronic Periodontitis in a Chinese Population", Journal of Periodontology, vol. 80, No. 4, pp. 603-608, 2009.
Warren, J.J., et al., "A review of fluoride dentifrice related to dental fluorosis", Pediatr. Dent., vol. 21, No. pp. 265-271, Jul.-Aug. 1999.
Wilkinson, E.G., et al., "Bioenergetics in clinical medicine. II. Adjunctive treatment with coenzyme Q10 in periodontal therapy", Res. Com. Chem. ath. Pharm. vol. 12, No. 1, p. 111-123, 1975.
Wilkinson, E.G., et al., "Bioenergetics in clinical medicine. VI. Adjunctive treatment of periodontal disease with coenzyme Q10", Res. Com. Chem. Path. Pharm., vol. 14, No. 4, pp. 715-719, 1976.
Wu, L.C., et al., "Anti-inflammatory effect of spilanthol from Spilanthes acmelia on murine macrophage by down-regulating LPS-induced inflammatory mediators", J. Agric. Food Chem., vol. 56, No. 7, pp. 2341-2349, Apr. 9, 2008 (Apr. 9, 2008), Abstract.
Zero, D.T., "Dentifrices mouthwashes, and remineralization/caries arrestment strategies", BMC Oral Health, vol. 6 (Suppl 1), No. 59, pp. 1-13.
Attin, T., et al., "Deposition of fluoride on enamel surfaces released from varnishes is limited to vicinity of fluoridation site", Clin Oral Investig, vol. 11, pp. 83-88, 2007.
Bashutski, J.D., et al., "The Impact of Vitamin D Status on Periodontal Surgery Outcomes", J. Dent. Res., vol. 90, No. 8, pp. 1007-1012, 2011.
Beltran-Aguilar, E.D., et al., "Fluoride varnishes: A review of their clinical use, cariostatic mechanism, efficacy and safety", JADA, vol. 131, pp. 589-594, 2000.

(56) References Cited

OTHER PUBLICATIONS

Caslavska, V., et al., "CaF2 in Enamel Biopsies 6 Weeks and 18 Months after Fluoride Treatment", Caries Res, vol. 25, pp. 21-26, 1991.
Chantal, J., et al., "The coming of age of 1,25-dihydroxyvitamin D3 analogs as immunomodulatory agents", Trends Mol Med., vol. 8, No. 4, pp. 174-179, 2002.
Chow, L.C., et al., "Apatitic fluoride increase in enamel from a topical treatment involving intermediate CaHPO4.2H2O formation, an in vivo study", Caries Res., vol. 15, pp. 369-376, 1981.
Christoffersen, J., et al., "Kinetics of dissolution and growth of calcium fluoride and effects of phosphate", Acta Odontol Scand, vol. 46, No. 6, pp. 325-336, 1988.
Crall, J.J., et al., "Enamel fluoride retention after DCPD and APF application and prolonged exposure to fluoride in vitor", J. Dent Res, vol. 65, No. 3, pp. 387-389, 1986.
Cruz, R., et al., "Uptake of KOH-soluble and KOH-insoluble fluoride in sound human enamel after topical application of a fluoride varnish (Duraphat) or a neutral 2% NaF solution in vitro", Scand J Dent Res., vol. 100, No. 3, pp. 154-158, 1992.
Diamond, G., et al., "Host defense peptides in the oral cavity and the lung: similarities and differences", J. Dent. Res., vol. 87, No. 10, pp. 915-927, 2008.
Dietrich, T., et al., Association between serum concentrations of 25-hydroxyvitamin D and gingival inflammation1'2'3', Am. J. Clin. Nutr., vol. 82, No. 3, pp. 575-580, 2005.
Dijkman, A.G., et al., "In vivo investigation on the fluoride content in and on human enamel after topical applications", Caries Res., vol. 17, pp. 392-402, 1983.
Dixon, D., et al., "Calcium and vitamin D use among adults in periodontal disease maintenance programmes", British Dental Journal, vol. 206, No. 12, pp. 627-631, 2009.
Dudev, T., et al., "Monodentate versus bidentate carboxylate binding in magnesium and calcium proteins: what are the basic principles?", J. Phys. Chem. B., vol. 108, pp. 4546-4557, 2004.
Featherstone, J.D., "Prevention and reversal of dental caries: role of low level fluoride", Community Dent Oral Epidemiol, vol. 27, pp. 31-40, 1999.
Featherstone, J.D.B., "The Science and Practice of Caries Prevention", Journal of the American Dental Association, vol. 131, pp. 887-899, 2000.
Folkers, K., "A critique of 25 years of research which culminated in the successful therapy of periodontal disease with coenzyme Q10", J. Dent. Health, vol. 42, pp. 258-263, 1992.
Garcia, M., et al., "One-Year Effects of Vitamin D and Calcium Supplementation on Chronic Periodontitis", Journal of Periodontology, vol. 82, No. 1, pp. 25-32, 2011.
Gombart, A.F., "The vitamin D-antimicrobial peptide pathway and its role in protection against infection", Future Microbiology, vol. 4, No. 9, pp. 1151-1165, 2009.
Hanioka, et al., "Effect of Topical Application of Coenzyme Q10 on Adult Periodontitis", Molec. Aspects of Med., vol. 85 (Supplement), pp. S241-S248, 1994.
Hansdottir, S., et al., "Vitamin D Decreases Respiratory Syncytial Virus Induction of NF-κB-Linked Chemokines and Cytokines in Airway Epithelium While Maintaining the Antiviral State", The Journal of Immunology, vol. 184, No. 2, pp. 965-974, 2010.
Helfenstein, U., et al., "Fluoride varnishes (Duraphat): A meta-analysis." Community Dent Oral Eipdemiol, vol. 22, pp. 1-5, 1994.
Kishi, T., et al., Journal of Dental Health, vol. 43, pp. 667-672, 1993.
Miley, D.D., et al., "Cross-sectional study of vitamin D and calcium supplementation effects on chronic periodontitis", J. Periodontol, vol. 80, No. 9, pp. 1433-1439, Sep. 2009.
Ernster, L., et al., "Ubiquinol: an endogenous antioxidant in aerobic organisms", Clinical Investigator, vol. 71, pp. S60-S65, 1993.
Nakamura, R., et al., "Deficiency of Coenzyme Q in Gingiva of Patients with Periodontal Disease", Internal. J.Vit. Nutr. Res., vol. 43, pp. 84-92, 1973.
Vogel, G.L., et al., "Salivary fluoride from fluoride dentifrices or rinses after use of a calcium pre-rinse or calcium dentifrice", Caries Res., vol. 40, pp. 449-454, 2006.
Wang, X.L., et al., "Cosupplementation with vitamin E and coenzyme Q10 reduces circulating markers of inflammation in baboons1-3", Am. J. Clin. Nutr., vol. 80, No. 3, pp. 649-655, Sep. 2004.
Wu, L.C., et al., "Anti-inflammatory effect of spilanthol from Spilanthes acmelia on murine macrophage by down-regulating LPS-induced inflammatory mediators", J. Agric. Food Chem., vol. 56, No. 7, pp. 2341-2349, Apr. 9, 2008 '(Apr. 9, 2008), Abstract.
European Search Report issued in EP Application No. EP15777496.9 dated Oct. 30, 2017.
Anonymous: "Enamelon Preventive Treatment (gel) Premier Dental Products Company", Jan. 1, 2014, Retrieved from the Internet: URL:https://www.drugs.com/otc/130495/enamelon-preventive-treatment.html.
Supplementary European Search Report issued in EP Application No. EP15776096.8 dated Oct. 24, 2017.

\* cited by examiner

TOPICAL VITAMIN D AND UBIQUINOL ORAL SUPPLEMENT COMPOSITIONS

RELATED APPLICATIONS

The subject application is a continuation-in-part of a U.S. patent application entitled: "TOPICAL VITAMIN D ORAL SUPPLEMENT COMPOSITIONS", filed on Oct. 12, 2012, which claims priority from U.S. Provisional Application Ser. No. 61/546,811 titled Dental Floss Containing Vitamin D Compound filed on Oct. 13, 2011, the entire content of which is incorporated by reference.

FIELD OF THE INVENTION

The subject application pertains to a topical vitamin D and UBIQUINOL supplement composition useful in treating oral inflammation and reducing oxidative stress.

BACKGROUND OF THE INVENTION

Recent research has shown that human gingival epithelial cells (GEC) produce peptides, such as defensins and the cathelicidin LL-37, which are both antimicrobial and modulate the innate immune response. See: Diamond, G, et. al. (2008) "Hold defense peptides in the oral cavity and the lung: similarities and differences," *J. Dent. Res.* 87:915-927. Research has also demonstrated that these antimicrobial peptides are crucial in the prevention and control of periodontal disease of a bacteriological etiology. Specifically, these peptides have been shown to provoke an increased immune response and demonstrate antibacterial activity in the presence of the periodontal pathogen *Aggregaitbacter actinomycetemcomitans*. It has also been demonstrated that the genes responsible for the production of these antimicrobial peptides can be up-regulated or induced to produce an increased expression of these protective agents in the presence of adjunctively administered vitamin D supplement, i.e. vitamin D3 [1,25(OH)2D3] and its precursors and derivatives. See: McMahone, L, et. al. (June 2011) "Vitamin D-mediated induction of innate immunity in gingival epithelial cells," *Infect. Immun.*, 79(6) 2250-7.

SUMMARY OF THE INVENTION

The present invention is directed to vitamin D and UBIQUINOL supplement mixtures in topical, oral compositions useful for treating oral inflammation and reducing oxidative stress.

Suitable vitamin D supplements for the purposes of the invention include:
Vitamin D,
Vitamin D compounds with hydroxyl groups at 1, 3 and 25 carbon positions, esters of 1α,25-dihydroxy vitamin $D_3$,
esters of 1,25-dihydroxy vitamin $D_3$,
$1,25(OH)_2D_3$ analogs of $1,25(OH)_2D_3$,
Calcitriol, $25(OH)D_3$, analogs of $25(OH)D_3$ and combinations thereof.

Stable UBIQUINOL supplements for the purposes of the present invention are represented by the following structural formula:

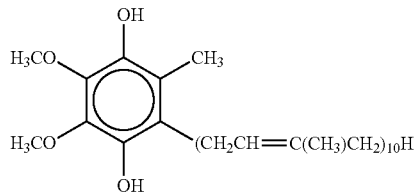

Suitable UBIQUINOL supplements for the purposes of this invention include a stabilizing composition comprising ascorbyl palmitate, propylene glycol and carboxymethylcellulose in a weight ratio to UBIQUINOL from between about 1.5 and 2.5.

The vitamin D and UBIQUINOL supplement mixture is contained in an aqueous-free emulsion along with trans-oral mucosal, absorption facilitators.

The present invention is directed to a topical, vitamin D and UBIQUINOL, oral supplement composition useful in treating oral inflammation and reducing oxidative stress, comprising:
  a saliva soluble, aqueous-free, emulsion carrier;
  an effective level of vitamin D and UBIQUINOL supplement mixture;
  a stabilizing composition for UBIQUINOL supplement;
  spilanthes extract and a trans-oral mucosal, absorption facilitator, wherein:
    upon application to the oral mucosa, said composition forms a saliva soluble, mucoadhesive gel, substantive to said oral mucosa;
    upon continuous exposure of said saliva soluble, mucoadhesive gel to saliva flow, said mucoadhesive gel gradually dissolves effecting controlled release of said vitamin D and UBIQUINOL supplement mixture, said trans-oral mucosal, absorption facilitator and spilanthes extract onto said oral mucosa; and
    upon contacting said oral mucosa, said vitamin D and UBIQUINOL supplement mixture, trans-oral mucosal, absorption facilitator and spilanthes extract passively diffuse through said oral mucosa:
      (a) regulating the in vivo availability and immune response of vitamin D and UBIQUINOL;
      (b) maintaining adequate levels of circulating vitamin D and UBIQUINOL; and
      (c) minimizing risk of hypercalcemia.

Vitamin D and UBIQUINOL supplement compositions of the invention, when topically applied to the oral mucosa in aqueous-free, emulsion compositions, form gels substantive to the oral mucosa. These gels gradually dissolve in the presence of saliva, releasing vitamin D and UBIQUINOL, with its stabilizing composition, trans-oral mucosal, absorption facilitators and spilanthes extract which, combined, effect passive diffusion of the vitamin D and UBIQUINOL supplement through the oral mucosa.

Incipient periodontal inflammation, gingivitis, is known to result from the inflammation reaction to the endotoxins released by the presence of bacterial biofilms in the general area of the tooth anatomy. Left untreated, this condition frequently progresses to the more virulent pathological condition known as periodontitis. It is believed that the frequent use of vitamin D, topical, supplement compositions of the invention provides protection by forming mucoadhesive gels that continuously release vitamin D composition at the inflamed site; thereby inducing passive diffusion of vitamin D into the mucosa which, in turn, increases production of the antimicrobial peptides and provokes a putative therapeutic immune modulating response. Simultaneously, the passive diffusion of UBIQUINOL supplement into the mucosa, reduces oxidative stress associated with oral inflammation.

The diffused vitamin D supplement mixture and UBIQUINOL maintain adequate levels of circulating vitamin D and UBIQUINOL, and regulates the in vivo availability and immune response of vitamin D and UBIQUINOL, while minimizing the risk of hypercalcemia.

The Role of Vitamin D in Maintaining Periodontal Health in the Compositions of the Invention Periodontal diseases are initiated by a consortia of oral bacteria that elicit local inflammatory responses that lead to bleeding on probing, loss of periodontal attachment, as well as bone and tooth loss. They have been linked to systemic conditions, including heart disease, diabetes, obesity and metabolic syndrome. The association between periodontal diseases and these systemic conditions seems to be due to a low grade inflammatory burden that links them through a common pathophysiological mechanism. Conceivably, locally secreted cytokines and periodontal pathogens can enter into the bloodstream and contribute to damage elsewhere in the body and there appears to be some evidence for that burden.

Tumor necrosis factor α (TNF-α) and interleukin 6 (IL-6) are key cytokines in the initiation and maintenance of systemic inflammation which have been implicated in progression and severity of periodontitis. In addition, higher serum levels of these cytokines have been observed in periodontitis patients than in periodontally healthy individuals.

Leptin, adiponectin and resistin are adipokines that are secreted primarily by adipose tissues, but also produced by monocytes and macrophages and are able to directly influence inflammation. See: Teles, et. al. *Journal of Periodontology*, 2011.

Vitamin D has an important role in bone growth and maintenance, which might be beneficial for maintaining periodontal health. Recently, it has been suggested to have positive effects on periodontal diseases, tooth loss and gingival inflammation not through its effects on bone metabolism, but rather through anti-inflammatory mechanisms. Hence, maintaining adequate serum values of Vitamin D via topical, adjunctive, vitamin D supplement compositions could be important in the prevention and treatment of periodontal diseases.

Vitamin D has an important role in calcium homeostasis, bone growth and preservation. It has been shown to inhibit antigen-induced T cell proliferation and cytokine production, acting as an immunomodulatory agent.

Recently, vitamin D has been proposed to also have anti-inflammatory properties. Analyzing 6,700 subjects (See: Dietrich, et. al., *Am. J. Clin. Nutr.* 2005, 82:575-580) found that individuals in the highest quintile of serum vitamin D presented significantly less bleeding, lower mean pocket depth and clinical attachment loss, number of missing teeth and BMI. It has also been suggested that vitamin D (and calcium) oral supplementation may have a positive effect on periodontal health, particularly on bleeding on probing, gingival index and PD. See: Garcia, et. al. *J. Periodontol.* 82:25-32; and Miley. et. al. *J. Periodontol.*, 2009; 80:1433-1439.

Interestingly, polymorphisms in vitamin D receptors have been linked to generalized aggressive periodontitis (GAgP) (see: Park, et. al. *J. Clin. Periodontol.* 2006; 33:524-528) and severe chronic periodontitis (see: Wang, et. al. *J. Periodontol.* 2009; 80:603-608). The highest levels of circulating vitamin D were detected among the individuals that presented less bleeding on probing, lower mean PD, CAL and number of missing teeth, as well as levels of pathogenic bacteria. In addition, the proposed anti-inflammatory role of vitamin D was confirmed by its positive correlation with adiponectin and negative correlation with IL-6 and leptin.

The active form of vitamin D, 1,25-dihydroxyvitamin D3 [1,25(OH)2D3], is a secosteroid hormone that regulates calcium and bone metabolism, controls cell proliferation and differentiation and exerts immunoregulatory activities. This range of functions has been exploited clinically to treat a variety of conditions, from secondary hyperparathyroidism to osteoporosis, to autoimmune diseases such as psoriasis. Recent advances in understanding 1,25(OH)2D3 functions and novel insights into the mechanisms of its immunomodulatory properties suggest a wider applicability of this hormone in the treatment of oral inflammation.

The di-hydroxylated, biologically active form of vitamin $D_3$, also known as calcitriol, is a central hormone in calcium homeostasis and bone metabolism, but has also a number of other functions and notably powerful immunomodulatory properties, which are attractive for adjunctive, topical supplementation.

U.S. Pat. No. 5,952,317, discusses calcitiol derivatives and their uses. Calcitriol can be regulated to thus provide controlled release of vitamin D in vivo over time, by changing or modifying the hydrolysable groups. Structurally, the key feature of the modified vitamin D compounds having desirable biological attributes is that they are derivatives of 25-dihydroxyvitamin D3, or derivatives of 25-dihydroxyvitamin D analogs, in which a hydrolysable group is attached to the hydroxyl group of carbon 25 and, optionally, to any other of the hydroxyl groups present in the molecule. Depending on various structural factors, e.g. the type, size, structural complexity of the attached group, these derivatives are thought to hydrolyze to 25-dihydroxyvitamin D3, or to a 25-dihydroxyvitamin D3 analog, at different rates in vivo, thus providing for "slow release" of the biologically active vitamin D compound (i.e. 1,25-dihydroxyvitamin D3, or an analog thereof) in the body. The "slow release" in vivo activity profiles of such compounds can be further modulated by the use of mixtures of derivatives (e.g. mixtures of different derivatives of 1,25-dihydroxyvitamin D3, or different derivatives of 1,25-dihydroxyvitamin D analogs) or the use of mixtures consisting of one or more vitamin D derivatives together with chemically modified molecules derived from 1,25(OH)2D3. Modifications have been made throughout the molecule to obtain analogs with the desired properties. More than 1000 different vitamin D analogs have been synthesized worldwide. All of these analogs fall within the description of vitamin D, as discussed and claimed in the present invention.

Vitamin D receptor (VDR): a member of the superfamily of nuclear receptors for steroid hormones and retinoid acid. The VDR functions as a 1,25(OH)$_2$D3-activated transcription factor that ultimately influences the rate of RNA polymerase mediated transcription. VDRs are present not only in cells typically involved in calcium and bone metabolism, but also in other cell types, such as cells of the immune system. See: Chantal Mathieu and Luciano Adorini. "The coming age of 1,25-dihydroxyvitamin D3 analogs as immunomodulatory agents," *TRENDS in Molecular Medicine*. Vol 8, No 4, April 2002.

An immunomodulatory role for vitamin D was first proposed more than 25 years ago, based on two salient observations. Firstly it was shown that monocytes/macrophages from patients with the granulomatous disease, sarcoidosis, constitutively synthesize the active form of vitamin D, 1,25-dihydroxyvitamin D (1,25(OH)$_2$D) from precursor 25-hydroxyvitamin D (25OHD). Secondly, the receptor for 1,25(OH)$_2$D (vitamin D receptor, VDR) is detectable in activated, proliferating lymphocytes. These observations suggested a mechanism whereby 1,25(OH)$_2$D produced by monocytes could act upon adjacent T-cells or B-cells, but the impact of such a system on normal immune system regulation was uncertain. Indeed, it is only in recent years that a much clearer picture of the role of vitamin D as a determinant of immune responsiveness has emerged. Two new concepts have prompted this change. Firstly studies of innate immunity have shown that intracine induction of antimicrobial activity by vitamin D is a pivotal component of monocyte/macrophage response to infection. Secondly, it is now clear that sub-optimal vitamin D status is a common feature of many populations throughout the world, with the potential to compromise monocyte/macrophage metabolism of 25OHD and subsequent actions of 1,25(OH)$_2$D. More recent reviews detail these new developments with specific reference to the metabolic and signaling mechanisms associated with innate immune regulation by vitamin D and implications for human disease, including oral inflammation. See: Martin Hewison, "Review: Vitamin D and the intracrinology of innate immunity," *Molecular and Cellular Endocrinology* 321 (2010) 103-111.

In a recent review of this subject Holick (2007) *N. Engl. J. Med.,* 357:266-281, indicated that vitamin D insufficiency could be characterized by circulating levels of 25OHD that were greater than vitamin D-deficiency (50 nM or 20 ng/ml) but less than 75 nM (30 ng/ml). See: Holick 2009, *Ann. Epidemiol.* 19: 73-7.

Thus, for the first time since the original sarcoidosis studies it is possible to propose a mechanism detailing the benefits of intracine metabolism of 25OHD with respect to innate immune response to infection by monocyte/macrophages. In the face of an immune challenge such as infection with M.tb. pathogen-sensing receptors such as TLRs trigger enhanced expression of 1α-hydroxylase and VDR. Provided there is sufficient 25OHD available, this will then elevate local levels of 1,25(OH)$_2$D, stimulating transcription of the hCAP gene, with the resulting antimicrobial protein being incorporated into lysosomes to promote bacterial killing. Initially hCAP was thought to act primarily by disrupting bacterial cell membranes. See: Nizet and Gallo, *Scan. J. Infect. Dis.,* 2003; 35:670-676.

A new perspective on the interaction between vitamin D and human immunity has shed light on the intracrine mechanisms that are central to its immunomodulatory activity. Crucially it is now clear that these mechanisms are also common to cells from a variety of tissues outside the classical immune system, notably "barrier" sites such as the skin, lungs, intestine, placenta and oral mucosa. Irrespective of the cell type involved in mediating intracrine responses to vitamin D, these studies have underlined the potential problems that may stem from inadequate vitamin D status. The latter appears to be a prevalent condition in communities throughout the world, further emphasizing the need for new clinical studies aimed at assessing the physiological and disease consequences of vitamin D insufficiency and the potential for topical administration of vitamin D supplement to local inflammatory conditions, as described and claimed by the present invention.

Vitamin D deficiency has been correlated with increased rates of infection. Since the early 19$^{th}$ century, both environment (i.e. sunlight) and dietary sources of vitamin D (i.e. cod liver) have been identified as treatments for TB. The recent discovery that vitamin D induces antimicrobial peptide gene expression explains, in part, the "antibiotic" effect of vitamin D and has greatly renewed interest in the ability of vitamin D to improve immune function. Subsequent work indicates that this regulation is biologically important for the response of the innate immune system to wound and infection, including oral infections, and that deficiency may lead to suboptimal responses toward bacterial and viral infections. The potential for topical supplementation of vitamin D to respond to oral inflammation is most promising.

25(OH)D circulates in the blood bound to the vitamin D-binding protein and is a reliable indicator of vitamin D status. To become fully activated, the 25(OH)D is converted into 1,25-dihydroxyvitamin D(1,25(OH)2D) by the mitochondrial 1α-hydroxylase enzyme (CYP2781). The majority of the body's 1,25(OH)2D is synthesized in the primary renal tubules of the kidney, but the synthesis also occurs in numerous extrarenal site by to cells that express CYP2781.

The genomic actions of 1,25(OH)2D are modulated through the vitamin D receptor (VDR), a transcription factor belonging to the steroid/hormone receptor family.

Deficiency in vitamin D is associated with numerous health conditions ranging from bone health to cancer, but with the discovery of antimicrobial peptide gene regulation by the vitamin D pathway, a renewed interest in its impact on the immune system has ensued. It is particularly attractive to realize that adequate vitamin D levels throughout life may alleviate many of the chronic ills that befall us as we age. "Local" vitamin D levels may be influenced by repetitive, topical administration of vitamin D supplement throughout the day.

Many epithelial tissues such as the oral mucosa, intestinal tract, skin, urinary tract and reproductive organs are constantly exposed to the environment and the importance of the vitamin-D-cathelicidin pathway in providing protection against pathogens in these tissues is already a major focus. This includes topical application of vitamin D supplement to the oral mucosa from compositions that effect continuous trans-oral, mucosal absorption throughout the day, as disclosed and claimed in the present invention.

Considering that most people have insufficient levels of vitamin D and that nearly 1 billion people worldwide are deficient, properly designed supplementation studies in humans will be important for determining the benefits from raising serum levels of vitamin D. See: Adrian F. Gombart. The Vitamin D-antimicrobial peptide pathway and its role in protection against infection. *Future Microbial.* (2009) 4(9): 1151-1166.

Vitamin D is known to modulate calcium homeostasis and has a role in the regulation of electrolytes and blood pressure. There is now an increasing amount of evidence to show that 1,25(OH)$_2$D$_3$, the most active metabolite of Vitamin D, regulates the immune response and possesses anti-inflammatory activity. See: *Current Opinion in Gastroentarology.* 2010; 26:591-595.

Significant advances have been made in the characterization of Vitamin D and the Vitamin D receptor (VDR) in immune function. The studies of signaling pathways involved in the response to infection and inflammation have led to a more detailed understanding of the cellular response to Vitamin D through VDR. The present invention is based on recent progress in understanding how Vitamin D topically administered to the oral mucosa contributes to mucosal immune function, particularly in relation to the molecular mechanisms by which Vitamin D and VDR influence mucosa-immunity, bacterial infection, and inflammation.

Recently, it was shown that Vitamin D modulates the T cell antigen receptor, further demonstrating that Vitamin D has a nonclassical role in immunoregulation. The anti-inflammation and anti-infection functions for Vitamin D are newly identified and highly significant activities relied on by the topical, vitamin D supplement compositions of the invention. Vitamin D/VDR have multiple critical functions in regulating the response to intestinal homeostasis, tight junctions, pathogen invasion, commensal bacterial colonization, antimicrobe peptide secretion and oral mucosal defense. Interestingly, microorganisms modulate the VDR signaling pathway.

Vitamin D is known as a key player in calcium homeostasis and electrolyte and blood pressure regulation. Recently, important progress has been made in understanding how the noncanonical activities of Vitamin D influence the pathogenesis and prevention of human disease. Vitamin D and VDR are directly involved in T cell antigen receptor signaling. The involvement of Vitamin D/VDR in anti-inflammation and anti-infection represents a newly identified and highly significant activity for VDR. Studies have indicated that the dysregulation of VDR may lead to exaggerated inflammatory responses, raising the possibility of defects in Vitamin D and VDR signaling transduction may be linked to bacterial infection and chronic inflammation including periodontitis.

Overall, the effects of $1,25(OH)_2D_3$ on the immune system include: modulating the TCR, decreasing Th1/Th17CD4+ T cells and cytokines, increasing regulatory T cells, down-regulating T cell-driven production and inhibiting dendritic cell differentiation.

Consistent with its anti-inflammatory role, $1,25(OH)_2D_3$ downregulates the expression of many proinflammatory cytokines, such as IL-1, IL-6, IL-8 and TNF-α, in a variety of cell types. Immune cells, including macrophages, dendritic cells and activated T cells, express the intracellular VDR and are responsive to $1,25(OH)_2D_3$.

Vitamin D deficiency has been correlated with increased rates of infection. Moreover, $1,25(OH)_2D_3$ induces the expression of antimicrobial peptides, such as carhelicidin. Thus, recent studies have greatly renewed interest in the anti-infection activity of $1,25(OH)_2D_3$ for use in the topical supplement compositions of the invention. See: Gombert A. F. *Future Microbial.* 2009; 4:1151-1165.

Manipulating the level of $1,25(OH)_2D_3$ in the body and restoring the function of VDR via topical supplementation represent a new approach to treating periodontitis relied on by the topical supplement compositions of the invention. $1,25(OH)_2D_3$ has potent immunomodulatory properties that have promoted its potential use in the prevention and treatment of infectious disease, including periodontitis. See: Newsson M. *Mol. Cell Endocrinol.* 2010; 321:103-111.

Vitamin D deficiency at the time of periodontal surgery negatively affects treatment outcomes for up to 1 year. Analysis of data suggests that vitamin D status may be critical for post-surgical healing. (Clinical)Trials.gov number, CT00277065.

The primary sources of vitamin D are dietary intake and sunlight exposure in the form of vitamin D2 and D3, which are metabolized to 25-hydroxyvitamin D [25(OH)D] in the liver. Further metabolism in the kidneys produces the active form of vitamin D, 1,25-dihydroxyvitamin D.

Periodontitis is characterized by alveolar bone loss induced by the host immune response in bacterial insult. Because vitamin D plays a crucial role in bone maintenance and immunity, there is biologic rationale to suspect that a vitamin D deficiency could negatively affect the periodontium. A diagnosis of vitamin D deficiency is made through serum analysis of 25(OH)D levels. The normal range of serum 25(OH)D levels is 20-74 ng/mL. No absolute threshold for deficiency status is universally accepted, although most authorities agree that levels below 20-30 ng/mL constitute at least a mild deficiency with severe vitamin D deficiency beginning at a level of 12 ng/mL. See: Bashutski, et. al. *J. Dent. Res.* 90(8). 1007-1012, 2011. Topical supplementation of vitamin D in the compositions of the invention, influence "local" vitamin D levels of cells under challenge.

In cross-sectional studies, low vitamin D levels have been associated with increased gingival inflammation, tooth loss, clinical attachment loss and material periodontal disease during pregnancy. Daily administration of vitamin D via topical supplement compositions of the invention are projected to increase "local" vitamin D levels.

Interestingly, vitamin D supplementation at the time of surgery fails to prevent the negative clinical outcomes associated with baseline deficiency. Patients were supplemented with a vitamin D for only a six-week period, and it takes up to 3 months for serum 25(OH)D levels to stabilize after vitamin D intake is increased. See Veith R, et. al. *Am. J. Clin. Nutr.* 2001 February; 73(2):288-94. Six-week vitamin D supplementation alone did not exert long-term effects, since serum 25(OH)D levels returned to baseline levels in placebo patients by 6 months.

Analysis of data suggests that if an individual is vitamin D-deficient, minimal benefits can be obtained from periodontal surgery. Furthermore, vitamin D supplementation at the time of surgery is unable to prevent this effect. Since vitamin D deficiency is highly prevalent, it may be advisable to ensure adequate vitamin D levels well in advance of periodontal surgery, to attain the best possible results. Oral vitamin D supplementation, combined with topical vitamin D supplement compositions of the invention, administered daily for an extended period prior to periodontal surgery, is recommended.

Epidemiological studies suggest that low vitamin D levels may increase the risk or severity of respiratory viral infections. One study examined the effect of vitamin D on respiratory syncytial virus (RSV)-infected human airway epithelial cells. Airway epithelium converts 25-hydroxyvitamin $D_3$ (storage form) to 1,25-dihydroxyvitamin $D_3$ (active form). Active vitamin D generated locally in tissues, is important for the nonskeletal actions of vitamin D, including its effects on immune responses. It was found that vitamin D induces ixBα, an NF-xB inhibitor, in airway epithelium and decreases RSV induction of NF-xB-driven genes such as IFN-β and CXCL10. It was further found that exposing airway epithelial cells to vitamin D reduced induction of IFN-stimulated proteins with important antiviral activity (e.g., myxovirus resistance A and IFN-stimulated protein of 15 kDa). In contract to RSV-induced gene expression, vitamin D had no effect on IFN signaling, and isolated IFN induced gene expression. Inhibiting NF-kB with an adenovirus vector that expressed a nondegradable form of IkBa mimicked the effects of vitamin D. When the vitamin D receptor was silenced with small interfering RNA, the vitamin D effects were abolished. Most importantly, it was found that, despite inducing 1 kBa and dampening chemokines and IFN-β, there was no increase in viral mRNA or protein or in viral replication.

It was concluded that vitamin D decreases the inflammatory response to viral infections in airway epithelium without jeopardizing viral clearance. This suggests that adequate vitamin D levels would contribute to reduced inflammation and less severe disease in RSV-infected individuals.

Vitamin D is increasingly recognized as a pluripotent hormone with functions that extend beyond its classical role in calcium homeostasis. Rapidly growing evidence from epidemiological and basic research studies reveals that vitamin D can modulate immune responses. Vitamin D deficiency is highly prevalent and has been associated with both increased risk of several inflammatory diseases and susceptibility to infections, including periodontitis. The localized tissue-specific generation of active vitamin D is thought to be a key component of nonclassical vitamin D functions that are relied on by the supplement compositions of the invention. Previously published data has shown that normal lung epithelium constitutively converts 25-hydroxyvitamin $D_3$ (storage form of vitamin D) to 1,25-dihydroxyvitamin $D_3$(1, 25D) (active form of vitamin D) and that the generation of active vitamin D is increased in the presence of viral infection.

Inflammation is an essential component of host defense; however, a too vigorous response against microbes or inflammation may be deleterious to the host, leading to impaired organ function. Vitamin D has been shown to inhibit production of inflammatory chemokines in animal models of inflammatory diseases such as multiple sclerosis and type 1 diabetes.

The family of NF-kB transcriptional regulatory factors has a central role in coordinating the expression of a wide variety of genes that control immune responses. NF-kB proteins are present in the cytoplasm in association with 1xBs. IxBs are phosphorylated by 1xB kinase following cell stimulation, and they are targeted for destruction by the ubiquitin/proteasome degradation pathway. The degradation of 1xB allows NF-kB proteins to translocate to the nucleus, bind to their DNA binding sites and activate a variety of genes. See: Sif Hansdottir, et. al., *The Journal of Immunology.* 2010; 184: 965-974.

The hormonal form of vitamin D up-regulates antimicrobial peptides, namely cathelicidin, to enhance clearance of bacteria at various barrier sites and in immune cells. Vitamin D modulates the adaptive immune system by direct effects on T cell activation and on the phenotype and function of antigen-presenting cells (ACPs), particularly of DCs.

The importance of vitamin D on the regulation of cells in the immune system has gained increased appreciation over the past decade with the discovery of the vitamin D receptor (VDR) and key vitamin D metabolizing enzymes expressed by cells of the immune system. Animal studies, early epidemiologic and clinical studies have supported a potential role for vitamin D in maintaining immune system balance.

It is currently believed that vitamin D enhances innate immunity by up-regulating antimicrobial peptides such as cathelicidin in response to infection. This up-regulating of antimicrobial peptides is relied on by the topical supplement compositions of the present invention.

Therefore, antimicrobial peptides such as cathelicidin constitute an integral part of the innate immune response to a variety of infections especially at barrier sites, such as oral mucosa.

Taken together, these findings suggest that 1,25(OH)$_2$D$_3$ up-regulates antimicrobial peptide production, primarily cathelicidin, on a variety of different cells and can be relied on in the vitamin D supplement compositions of the invention.

In summary, the effects of 1,25(OH)$_2$D on the immune system include decreasing Th1/Th17 CD4+ T cells and cytokines, increasing regulatory T cells, downregulation of T cell-driven IgG production and inhibition of dendritic cell differentiation. While enhancing protective innate immune responses, 1,25(OH)$_2$D helps maintain self-tolerance by dampening overly zealous adaptive immune responses. See: Diane L. Kamen and Via Taagpricha. Vitamin D and molecular actions on the immune system: modulation of innate and autoimmunity. *J. Mol. Med.* (2010) 88:441-450.

Vitamin D, administered by the topical supplement compositions of the invention, may be beneficial for the treatment of periodontal disease, an inflammatory condition involving activation of host-defense cells by bacterial release of inflammatory mediators, which results in the destruction of supporting periodontal tissues, including connective tissue and alveolar bone.

Third National Health and Nutrition Examination Survey (NHANES III), which included 12,000 adults, revealed significant associations between periodontal health and vitamin D and calcium intakes. Thus, data from this large cohort would support the hypothesis that lower dietary intakes of vitamin D and calcium may contribute to poor periodontal health in a dose-dependent fashion.

Periodontal health improves in patients attending regular periodontal care programs, regardless of their dietary calcium or vitamin D supplements. However, taking calcium and vitamin D supplementation is associated with better periodontal health relative to taking no such supplements. Previous reports had suggested that vitamin D may reduce the susceptibility to gingival inflammation through anti-inflammatory effects, and one study demonstrated an inverse linear association between 25(OH)D and BOP. Consistent with this report, we observed less BOP and less inflammation in supplement takers, a difference that was evident at baseline and remained significant for 1 year while subjects underwent periodontal maintenance therapy. It should be noted that because of the inclusion of different covariates, the results of baseline analysis reported here are slightly different from those reported previously in the same population. See: M. Nathalia Garcia, et. al. One-Year Effects of Vitamin D and Calcium Supplementation on Chronic Periodontitis. *J. Periodontol.* 2011; 82:25-32.

Optimal levels of vitamin D should have an immunosuppressive effect on periodontal disease. See: D. Dixon, et. al. Calcium and vitamin D use among adults in periodontal disease maintenance programmes. *British Dental Journal.* 2009: 208:827-831.

In addition to its action on skeletal homeostasis, vitamin D and, in particular, its hormonally active form, 1α,25-dihydroxyvitamin D, has anti-inflammatory and antimicrobial effects via modulation of inflammatory cytokine production by immune cells and stimulated secretion of peptides with antibacterial action by cells of the monocyte-macrophage lineage. These properties lend themselves to topical supplement compositions for treatment of "local" oral infections.

All of the clinical and radiographical measurements indicate better periodontal health for subjects who took oral vitamin D and calcium supplementation. Furthermore, because all of the subjects were enrolled in periodontal maintenance programs, the data are consistent with the notion that taking vitamin D and calcium supplements may be beneficial effects above and beyond those of standard periodontal care.

Results suggest that vitamin D and calcium supplementation could be advocated as a component of periodontal disease management. See: D. Douglas, et. al., *J. Periodon-*

*tol.* September 2009; 80:1433-1439. Supplementation includes: topical supplements applied repetitively throughout the day.

Resulting recommendations vary widely. However, vitamin D likely has beneficial effects on various outcomes other than bone health, such as muscle strength, colon cancer and inflammatory diseases. In the present study, we did not find evidence for a threshold serum concentration of 25(OH)D, above which the association with gingival inflammation leveled off. Hence, the anti-inflammatory effects of vitamin D may possibly extend to serum concentration of 90-100 nmol/L. These results are consistent with an anti-inflammatory effect of vitamin D on gingival inflammation which may be an alternative pathway by which vitamin D may be beneficial for the prevention of periodontal disease.

Vitamin D, topical supplementation, by the compositions of the invention, may reduce susceptibility to gingival inflammation through its anti-inflammatory effects. Gingivitis may be a useful clinical model to evaluate the anti-inflammatory effects of topical vitamin D supplement compositions. See: Thomas Dietrich, et. al. *Am. J. Clin. Nutr.* 2005; 82-575

All of the foregoing references are hereby incorporated in their entirety by reference into the present invention.

The Role of UBIQUINOL in Reducing Oxidative Stress in the Compositions of the Present Invention CoQ10 is a fat soluble, essential, quinone molecule, found in every cell, tissue and organ in the body. CoQ10 partners with other enzymes in the body and plays a vital role in cellular and bodily health, including: energy production and free radical production. CoQ10 production in the body decreases with aging. CoQ10 has been shown to have antioxidant potential and to promote ATP production in the mitochondria inner membrane.

Oxidized (ubiquinone) and reduced (ubiquinol) forms have been identified for CoQ10. Ubiquinone is converted by NADPH-dependent CoQ10 reduction, which uses NADPH as an electron donor, into UBIQUINOL. UBIQUINOL is known to exist as the active form of the coenzyme in the body. In a study in which ubiquinone was orally administered to rats, most CoQ10 molecules detected from the lymph were in the form of UBIQUINOL, suggesting that the coenzyme is reduced immediately after being absorbed from the intestinal tract. UBIQUINOL molecules circulating in the body are incorporated into lipoproteins in the liver and are distributed to tissues all over the body via the blood stream.

These molecules appear to be converted to oxidized molecules in the blood when exposed to oxidative stress caused by various factors. However, since the ubiquinone molecules are re-reduced in the liver, over 90% of all CoQ10 molecules present in the blood of a healthy person are in the form of UBIQUINOL, suggesting that the molecules are in a strong reduction condition.

It is well established that CoQ10 (ubiquinone) is not well absorbed into the body, as has been published in many peer-reviewed, scientific journals. Since the reduced CoQ10 (ubiquinol) form has two additional hydrogens, it results in the conversion of two ketone groups into hydroxyl groups on the action portion of the molecule. This causes an increase in the polarity of the CoQ10 molecule and may be a significant factor behind the observed enhanced bioavailability of UBIQUINOL. Orally, UBIQUINOL exhibits greater bioavailability than ubiquinone: 150 mg per day of UBIQUINOL in a softgel resulted in peak blood values of 3.84 mcg/ml within 28 days. Reduced CoQ10 is absorbed faster and in a larger amount than oxidized CoQ10. See U.S. Pat. No. 6,184,255 assigned to KANEKA CORP.

Oxidative stress is detectable as changes in plasma CoQ10 concentrations and composition and plays an important role in oral inflammations experienced by "at-risk" patients. For example, deficiencies of Coenzyme Q10 (CoQ10), both oxidized (ubiquinone) and reduced (ubiquinol), have been implicated in: gums, gingiva and mucosa associated with gingivitis and periodontitis. "Local" oxidative stress is associated with oral inflammatory conditions experienced by "at-risk" patients, including mucostitis, stomatitis, thrush, etc.; and is the target of the topical oral supplement compositions of the invention.

UBIQUINOL is the first lipid soluble antioxidant available for antioxidant defenses in the mouth associated with oxidative stress. UBIQUINOL supplements applied topically to the oral mucosa, via aqueous-free emulsion compositions of the invention, would be the first lipid soluble, antioxidant response to oxidative stress in the oral cavity. In this regard, the plasma redox status of UBIQUINOL in the "local" systemic circulation of the oral cavity provides a measure of "local" systemic oxidative stress.

Adjunctive UBIQUINOL mediated effects on "local" oral inflammatory markers, with the topical supplement compositions of the invention, are expected to indicate reductions in the secretion of several pro-inflammatory cytokines. Damage to nuclear or mitochondrial DNA, indicated by mitochondrial dysfunction caused by biofilm oxidative stress is proposed as a common link among various oral inflammatory conditions.

Gingivitis and periodontitis are inflammatory disorders caused by bacteria living in biofilm. It is known that oxidative stress in the bloodstream and gingiva is increased by oral inflammatory disorders, including: gingivitis and periodontitis. The net effect of this oxidative stress . . . UBIQUINOL deficiencies, which are to be relieved with the compositions of the invention. See:

Littaru, et. al. "Deficiency of coenzyme Q10 in gingival tissue from patients with periodontal disease." (1971) *Proc. Nat. Acad. Science USA* 68:2332-2335.

Nakamura, et. al. "Deficiency of coenzyme Q10 in gingiva of patients with periodontal disease." (1973) *Int. J. Vit. Nut. Res.* 43:84-92.

Therapy of gum disease with UBIQUINOL and coenzyme Q10 (CoQ10) is reported by:

Folkers K (1992) "A critique of 25 years of research which culminated in the successful therapy of periodontal disease with coenzyme Q10." *J. Dent. Health* 42:258-263.

McCree, et. al. (1993) "Therapy with coenzyme Q10 for patients with periodontal disease.

Effect of coenzyme Q10 on subgingival microorganisms." *J. Dent. Health* 43:659-666.

Hanioka, et. al. "Effect of Topical Application of Coenzyme Q10 on Adult Periodontitis." (1994 *Molec. Aspects of Med.* Vo. 85 (Supplement) pp. S241-S248.

KANEKA Corp./Nihon University collaborative research on "Effect of the reduced form of coenzyme Q10 (ubiquinol) on oral environment for periodontal disease" presented by K. Sugawara and N. Sugano to: "The 63rd Meeting of the Vitamin Society in Japan" held Jun. 4 and 5, 2011 in Hiroshima.

It is well established that oral inflammations, including gingivitis an periodontitis, are accompanied by a deficiency of coenzyme Q10 (both oxidized and reduced versions).

Hanioka, et. al. (1994) topically applied CoQ10 once weekly via syringe to periodontal sites, for six weeks. The authors reported:
- "Tremendous improvement was found in bleeding on probing at CoQ10 treated sites after topical application was provided in combination with mechanical debridement."
- "Sites bled at day 0 showed no bleeding at six weeks. The effect of treatment was statistically significant only at experimental sites after mechanical subgingival debridement."
- "When topical application was provided as a sole treatment, periodontal probing depth, clinical attachment level and gingival crevicular fluid flow showed improvement only at CoQ10 treated sites."
- "Thus topical application of CoQ10 might enhance resistance of periodontal tissue to periodontopathic microorganisms."
- "improves adult periodontitis not only as a sole treatment but also in combination with traditional nonsurgical periodontal therapy."

However, the amount of CoQ10 absorbed in gingival tissue was not determined in this pilot study.

A June 2011, KANEKA/Nihon University presentation reports that oral administration of UBIQUINOL @ 150 mg capsule/day for two months "is effective in improving oral environment for periodontal disease."

Folkers K. (1992) states:
- "CoQ10 is, therefore, recommended for both prophylactic and therapeutic treatment of periodontal disease."
- "The indispensability of the intrinsic CoQ10 in boenergetics was emphasized as the basis for the extraordinary healing and the dental benefits resulting from the administration of CoQ10 to periodontal patients."
- "It was concluded that CoQ10 can improve bioenergetics and can be prophylactically and adjunctively used for extraordinary healing during routine periodontal therapy."
- "It was concluded that this CoQ10 therapy to reduce periodontal disease and particularly microorganisms is preferable to ordinary treatment with antibacterial agents because CoQ10 therapy improves the immune mechanisms to control disease."

From 1994 to date, extensive, published research by Kaneka Corp. on CoQ10 has established:
(a) an increased absorption rate into the bloodstream for reduced coenzyme Q10 (ubiquinol) compared to oxidized CoQ10 (ubiquinone);
(b) there are stability issues affecting UBIQUINOL availability when it is exposed to air and/or light;
(c) procedures have been developed for accurately monitoring plasma levels of ubiquinone and UBIQUINOL; and
(d) a shift in the proportions of subgingival microorganisms of periodontitis patients is attributed to UBIQUINOL adjunctive therapy. Note: This is a key finding for proposed relief of oxidative stress based on administering adjunctive UBIQUINOL aqueous-free emulsion compositions onto the oral mucosa, as described and claimed in the present invention.

Additional relevant references include:
Nylander M. and Nordlund M. (1991). Clinical effects on periodontal status after given oral supplement of ubiquinone. *Swed. J. Biol. Med.* 1, 6-11.
Wilkinson E. G., Arnold R. M., Folkers K., Hansen I. and Kishi H. (1975). Bioenergetics in clinical medicine. II. Adjunctive treatment with coenzyme Q10 in periodontal therapy. *Res. Com. Chem. Path. Pharm.* 12, 111-124.
Wilkinson E. G., Arnold R. M. and Folkers K. (1976). Bioenergetics in clinical medicine. VI. Adjunctive treatment of periodontal disease with coenzyme Q10. *Res. Com. Chem. Path. Pharm.* 13, 715-719.
Hanioka T., Tanaka M., Ojima M., Shizukulski S, and Folkers K. (1994). Effect of topical application of coenzyme Q10 on adult periodontitis. *Molec. Aspects Med.* Vol. 15 (Supplement) S241-S248.
Kishi T., et. al. (1993). *Journal of Dental Health.* 43:667-672.
Shimura Y., et. al. (1981). *Rinsho-to-Kenkyu,* 58, 1349-1352.
U.S. Pat. Nos. 7,897,169; 7,303,921; and 6,184,255.

Inflammation in General and UBIQUINOL SUPPLEMENT

The present invention is directed to relieving inflammation in the oral cavity that is usually accompanied by "oxidative stress" and reduced UBIQUINOL levels. Adjunctive UBIQUINOL supplement, topically applied by the compositions of the invention to the "local" oral mucosa, reduces oxidative stress while also effecting an anti-inflammatory effect as evidenced by reduced circulating markers of inflammation. See: X. Wang, et. al. *Am. J. Clinical. Nutr.* 2004, September; 80(3):649-655:
- "Co supplementation with Vitamin E and coenzyme Q10 reduces circulating markers of inflammation in baboons." Vitamin E may be added to the compositions of the present invention.
- "Inflammation and oxidative stress are processes that mark early metabolic abnormalities in vascular diseases.
  Dietary supplementation with Vitamin E reduces baseline inflammatory status indicated by the CRP concentrations in healthy baboons. Cosupplementation with CoQ10 significantly enhances this anti-inflammatory effect of Vitamin E."

Subsequent "inflammation" studies carried out with ubiquinol by C. Schmelzer, et. al. *J. Clin. Biochem. Nutr.* 44:62-66, January 2009, indicated:
- "In vitro effects of the reduced form of coenzyme Q10 on secretion levels of TNF-α and chemokines in response to LPS in the human monocytic celline THP-1"
- "In conclusion, our results indicate anti-inflammatory effects of the reduced form of CoQ10 on various inflammatory cytokines and chemokines in vitro."
- "Ubiquinol, the reduced form of coenzyme Q10 serves as a potent antioxidant of lipid membranes."

Topical administration of aqueous-free emulsion compositions of the invention form mucoadhesive gels in the presence of saliva, which continuously release stable UBIQUINOL supplement onto the oral mucosa, until the gel is dissolved by saliva. This controlled dosage is designed to maximize the therapeutic potential of UBIQUINOL by adjunctively restoring "local" UBIQUINOL deficiencies within circulating lipoproteins at systemic "uptake" rates. Multiple, topical doses of oral gels with aqueous-free emulsion/UBIQUINOL compositions of the invention, throughout the day; provide an ongoing adjunctive response to "local" UBIQUINOL deficiencies caused by oxidative stress. These multiple, topical doses are projected to be responsive to systemic UBIQUINOL uptake. Such a controlled, adjunctive, dosing response to local UBIQUINOL deficiencies caused by oxidative stress is not available from orally administered UBIQUINOL supplement using one or more capsules of UBIQUINOL daily.

Stable UBIQUINOL supplement's low water solubility (less than 0.1 mg/ml) and high molecular weight of 865, results in:
(1) slow absorption of UBIQUINOL supplement from the gastrointestinal tract, i.e. approximately 6 hours required to reach peak concentration, with
(2) steady-state concentrations reached within two weeks of treatment.

In contrast, topical, multiple dose administration of stable UBIQUINOL supplement compositions of the invention, from oral gels and once-a-day-flossing with a dental device, relies on ongoing trans-oral mucosal (sublingual) absorption to directly enter "local" systemic circulation (lymph system, bloodstream, gingiva, etc.). This alternative administration of stable UBIQUINOL supplement compositions of the invention avoids the "first-pass drug effect," which is experienced by orally administered drugs, where the drugs undergo metabolism. This "first pass drug effect" reduces the bioavailability of orally administered, stable UBIQUINOL supplement before it reaches systemic circulation. A therapeutic UBIQUINOL plasma level objective of >3.5 µg/ml is projected to be sufficient to reduce the secretions of pro-inflammatory cytokines in the oral cavity associated with oxidative stress. The level of systemic oxidative stress in the oral cavity can be established via the plasma redox status of UBIQUINOL.

Proposed advantages of multiple topical administrations of stable, UBIQUINOL supplement compositions of the invention from an oral gel, applied in repetitive doses throughout the day to "local" oral mucosa under oxidative stress; versus a single oral administration of a comparable quantity of stable UBIQUINOL supplement via capsule, include:

Efficiency of absorption increases as dose level decreases.
Bioavailability is optimized by avoiding "first-pass drug effect."
Maximum therapeutic potential of stable UBIQUINOL is achieved at a faster rate over a longer period of time.
"Local" UBIQUINOL systemic deficiencies are targeted directly vs. targeting UBIQUINOL deficiencies throughout the body.
Adjustments in topical administration can be made to accommodate varying UBIQUINOL plasma thresholds for different oral tissues.
Topical administration of stable UBIQUINOL supplement to the oral mucosa targets restoring "local" UBIQUINOL deficiencies via trans-oralmucosa absorption vs. oral administration of stable UBIQUINOL supplement, which undergoes trans-mucocal absorption in the small intestine and targets restoring UBIQUINOL deficiencies throughout the body.
A single, topical, "local" administration of 10 to 20 mg of stable UBIQUINOL supplement compositions of the invention from an oral gel extends over the life of the saliva soluble aqueous-free emulsions on the oral mucosa, i.e. 30 to 60 minutes. Such controlled release multiple dosages are responsive to stable UBIQUINOL supplement uptake in the systemic circulation and to the ongoing microflora challenge posed by oxidative stress. This is in contrast to the single oral administration of a 100 to 200 mg capsule of stable UBIQUINOL supplement.
Multiple, topical administrations of stable UBIQUINOL supplement locally, totaling between 50 and 200 mg carried out over an 8 to 12 hour period, is a more effective response to the continuing inflammatory challenge posed by oxidative stress. This extended topical administration is designed to optimize bioavailability while being responsive to local UBIQUINOL deficiencies attributed to continuing oxidative stress.

UBIQUINOL is considered to be the strongest lipid-soluble antioxidant that is biosynthesized, providing an active defense against oxidative insult to lipids, proteins and DNA.

UBIQUINOL supplement is unstable in the presence of oxygen, which has limited its use since its introduction in 2008 to oral capsules. R&D efforts, from 2008 to the present, by many companies attempting to stabilize UBIQUINOL for topical administration have been unsuccessful.

The present invention represents a major R&D and manufacturing breakthrough in the stabilization and dispensing of Kaneka QH™ UBIQUINOL supplement for Topical applications to the oral mucosa, for relief of oral discomfort attributed to dry mouth and oxidative stress.

The present invention relies on aqueous-free emulsion technology, which includes mucoadhesive properties, to transport Kaneka QH™ UBIQUINOL supplement to the oral mucosa for diffusion into the "local" circulatory system. Proprietary: formulating, processing and dispensing conditions for this combination: assures that the oxidative properties of Kaneka QH™ UBIQUINOL supplement have not been compromised and that "reduced" Kaneka QH™ UBIQUINOL is delivered topically to the oral mucosa.

Up to the present, restoration of UBIQUINOL deficiencies associated with dry mouth, has been primarily through adjunctive Kaneka QH™ UBIQUINOL supplement capsules administered orally. See references enclosed.

The "intensive care" ORAL GEL supplement compositions of the present invention rely on topical administration of UBIQUINOL/aqueous-free emulsions that form mucoadhesive gels on the mucosa. This proprietary, mucoadhesive gel continually releases:
(1) Spilanthes extract, to enhance saliva flow; and
(2) Kaneka QH™ UBIQUINOL supplement (in the reduced state), along with a trans-oral mucosal absorption facilitator.

The stabilized Kaneka QH™ UBIQUINOL supplement, in combination with its mucosal absorption facilitator, is continuously released from the mucoadhesive gel, followed by diffusion of UBIQUINOL supplement through the mucosa. The stabilized Kaneka QH™ UBIQUINOL supplement, combined with an absorption facilitator, enters the "local": bloodstream, lymph, gingiva and/or salivary glands via "passive diffusion" through the oral mucosa. This topical, adjunctive administration of UBIQUINOL "intensive care" ORAL GEL is projected to help: restore "local" UBIQUINOL deficiencies, increase saliva flow, restore salivary glands damaged by oxidative stress and provide relief from oral discomfort as discussed in the cited references.

This trans-oral mucosal absorption of Kaneka QH™ UBIQUINOL supplement, in the reduced state, continues until the mucoadhesive gel is dissolved by saliva. The substantivity of the mucoadhesive gel to the oral mucosa can be extended with various resin modifications to the mucoadhesive gel. For optimum results, multiple topical applications of UBIQUINOL "intensive care" ORAL GEL are recommended throughout the day.

Topical Oral Supplement Compositions of the Invention Feature

Kaneka QH™ UBIQUINOL SUPPLEMENT maintained in a proprietary, aqueous-free emulsion in a reduced state until the emulsion is exposed to saliva forming a mucoadhesive gel that is eventually solubilized by saliva and the UBIQUINOL supplement passively diffuses into the oral mucosa.

Topical, direct and rapid, adjunctive supplementation of "local", depleted, UBIQUINOL levels in the oral mucosa resulting in the restoration of a healthy redox balance.

Kaneka QH™ UBIQUINOL supplement, combined with an oral mucosal absorption facilitator, ensures rapid, optimal absorption and assimilation by the "local" oral mucosa.

Neutralizing free radicals in the local oral mucosa, thereby preventing cellular damage of the mucosa that would otherwise contribute to or exacerbate diseases of "intensive care" patients.

Providing the "local" oral mucosa, of "intensive care" patients, an ongoing active defense against oxidative insult to: lipids, proteins and DNA.

Helping relieve oral discomfort for those "intensive care" patients suffering from a range of oral conditions related to oxidative stress, including:
  dry mouth: xerostomia, Sjogren's disease, lupus, etc.;
  inflammation: gingivitis, periodontitis, periodontitis implantitis, mucositis, stomatitis, etc.;
  oral care specialist treatments by: periodontists, orthodontists, endodontists, oral surgeons, etc.;
  medical procedures for: cancer, diabetes, COPD, cardiovascular conditions, etc.; and/or
  various systemic conditions of "intensive care' patients, resulting in "free-radical-based" oxidative stress.

Topical Adjunctive Supplementation with the
Topical Supplement Compositions of the Invention
for "Intensive Care" Dry Mouth Patients Protect "local" oral mucosa cells with an extremely powerful antioxidant that features a strong protective defense against oxidative stress and dry mouth.

Not only effect: rapid, direct diffusion of UBIQUINOL SUPPLEMENT into the "local" oral mucosa; but also avoid the "first-pass effect" associated with orally administered Kaneka QH™ UBIQUINOL SUPPLEMENT capsules . . . while providing rapid, lasting, "local" relief from oral discomfort associated with oxidative stress and dry mouth.

Is considered a vital topical supplement for "intensive care" dry mouth patients seeking to maintain a healthy lifestyle.

All of the references cited herein, are hereby, in their entirety, incorporated by reference into the present invention.

DETAILED DESCRIPTION OF THE PRESENTLY PREFERRED EMBODIMENTS

In a preferred embodiment of the invention, vitamin D and UBIQUINOL supplement mixtures are included in a topical, oral supplement composition of the invention, where vitamin D supplement enhances innate immunity by upregulating the antimicrobial peptide, cathelicidin, and UBIQUINOL supplement reduces oxidative stress by increasing "local" UBIQUINOL levels.

In a particularly preferred embodiment of the invention, the topical, vitamin D, oral supplement, in its hormonally active form, 1α,25-dihydroxyvitamin D, indicates anti-inflammatory and antimicrobial effects via modulation of inflammatory cytokine production, by stimulating secretion of antibacterial properties; while UBIQUINOL reduces oxidative stress associated with inflammation by adjunctive supplementation of UBIQUINOL. The vitamin D supplement composition, in its hormonally active-form, 1α,25-dihydroxyvitamin D, calcitriol, indicates immunomodulatory properties; while UBIQUINOL supplement interferes with the inflammatory cascade, reducing oxidative stress via adjunctive supplementation of UBIQUINOL.

In another embodiment of the invention, the vitamin D supplement's anti-inflammatory and antimicrobial effects of 1α,25-dihydroxyvitamin D are modulated through vitamin D receptor (VDR).

In a preferred embodiment of the invention, vitamin D supplement, 1α,25-dihydroxyvitamin D, effect on the immune system includes:
  modulating TCR,
  decreasing TH1/TH17CP4 and T cells and cytokines
  increasing regulatory T cells
  down regulating T cell-driven production, and
  inhibiting dendritic cell differentiation The present invention includes methods:
  for treating oral inflammation and reducing oxidative stress, comprising administering topically a vitamin D and UBIQUINOL supplement mixture to the oral mucosa in a composition comprising:
  effective levels of a mixture of vitamin D and UBIQUINOL supplements;
  a saliva soluble, aqueous-free emulsion carrier for the supplement mixture;
  a stabilizing composition for UBIQUINOL comprising acorbyl palmitate, propylene glycol and carboxymetholcelluose in a weight-ratio to UBIQUINOL from between about 1.5 and 2.5;
  trans-oral mucosal, absorption facilitators; and
  spilanthes extract, where:
    upon application to the oral mucosa, said composition forms a saliva soluble, mucoadhesive gel, substantive to said oral mucosa;
    upon continuous exposure of said saliva soluble, mucoadhesive gel to saliva flow, said mucoadhesive gel gradually dissolves effecting controlled release of said vitamin D and UBIQUINOL supplement mixture, said trans-oral mucosal, absorption facilitators and spilanthes extract onto said oral mucosa;
  wherein application means for said topical vitamin D and UBIQUINOL oral supplement mixture composition is selected from the group consisting of interproximal devices coated with said composition, oral gels, oral ointments, oral pastes, oral varnishes, oral liquids, oral sealants, oral rinses, and combinations thereof;
  wherein treating oral inflammation comprises topically administering vitamin D and UBIQUINOL supplement mixture in a composition that is applied repetitively throughout the day with a vitamin D and UBIQUINOL supplement gel in combination with daily topical administration with a dental device coated with said composition containing vitamin D and UBIQUINOL supplement mixtures.

Vitamin D and UBIQUINOL compositions, suitable for topical administration to the oral mucosa, include: an aqueous-free emulsion carrier for the supplement mixture that also contains: a stabilizing composition for the UBIQUINOL, trans-oral mucosal absorption facilitators and spilanthes extract; wherein said aqueous-free emulsion, upon exposure to saliva, forms a mucoadhesive gel substantive to the oral mucosa. Upon saliva dissolution of this mucoadhesive gel, the vitamin D and UBIQUINOL mixture/trans-oral mucosal, absorption facilitator/spilanthes extract mixture gradually releases from the mucoadhesive gel to passively diffuse through the oral mucosa, thereby supplementing system serum levels of vitamin D, increasing UBIQUINOL levels.

Topical administration of the vitamin D and UBIQUINOL supplement mixtures in the combinations of the invention to the oral mucosa is preferably carried out with oral gels or dental devices coated with the vitamin D and UBIQUINOL mixture compositions. Particularly preferred, topical administration of the supplement mixture to the oral mucosa is effected by a combination of several administrations of the supplement mixture in a topical gel throughout the day, combined with once or twice daily flossing with a dental device composition coated with the vitamin D and UBIQUINOL supplement composition of the invention.

For purposes of the present invention, saliva soluble, aqueous-free emulsions include those emulsions that are comprised of polydimethylsiloxane in a nonionic surfactant, as described in the following U.S. Pat. Nos. 5,032,387; 5,098,711; 5,538,667 and 5,651,959; all of which are hereby incorporated by reference.

Preferred nonionic surfactants of the invention capable of forming a mucoadhesive gel in the presence of saliva. These are selected from the group consisting of: poloxamer 237, poloxamer 338, poloxamer 407 and combinations thereof.

For the purposes of the present invention, trans-oral mucosal, absorption facilitators are selected from the group consisting of: dexpanthenol, d-Limonene, poloxamer, PEG, benzyl alcohol, carbopol, chitosan, N-trimethylchitosan, menthol and combinations thereof.

Preferred aqueous-free, saliva soluble emulsions for use as carriers of THE vitamin D and UBIQUINOL supplement mixtures in the compositions of the present invention include emulsions of polydimethylsiloxane (PDMS) at viscosities ranging from between about 1500 cs and about 2.5 million cs. Particularly preferred, aqueous-free emulsions include as the discontinuous phase PDMS at viscosities between 10,500 cs and 2.5 million cs with those nonionic surfactants described in detail in U.S. Pat. No. 5,651,959, as the continuous phase.

Preferred polydimethylsiloxanes are selected from the group consisting of polydimethylsiloxane: at 1500 cs, at 12,500 cs, at 100,000 cs, at 250,000 cs, at 500,000 cs, at 750,000 cs, at 1.5 million cs, at 2.2 million cs, at 2.5 million cs and combinations thereof.

Preferred application means for the topical vitamin D and UBIQUINOL oral supplement compositions of the present invention include: oral gels, oral ointments, oral pastes, oral varnishes, oral liquids, oral sealants and oral rinses, and various interproximal devices coated with said topical vitamin D and UBIQUINOL oral supplement compositions.

Preferred oral gels for purposes of the present invention include those gels disclosed in U.S. Pat. Nos. 5,009,881; 5,032,387; 5,057,306; 5,057,307; 5,057,309; 5,538,667 and 5,651,959; all of which are included herein by reference.

Preferred coated, interproximal devices, suitable for releasing vitamin D and UBIQUINOL oral supplement compositions interproximally, include those interproximal devices described in the following U.S. Pat. Nos. 4,911,927; 4,942,034; 5,098,711; 5,165,913; 5,665,374; 5,711,935; 6,545,077; 6,575,176; 7,017,591; 7,025,986 and 7,152,611; all of which are hereby included by reference.

The use of dental devices is an extremely important adjunct to proper dental hygiene. Dental devices have long been used effectively to clean the spaces between the teeth and under the gingival margin. When used properly, dental devices have been found to be effective in inhibiting tooth decay and gum disease. They are recommended by dentists for daily dental hygiene.

To increase the effectiveness of the dental devices, some devices have included certain medicinal ingredients or dentifrice components to help protect the tooth enamel from acid attack. Bactericides have also been used in connection with dental floss to inhibit periodontal disease.

The vitamin D and UBIQUINOL supplement compositions on the dental devices of the invention can also be used in tandem and coated with salts containing ions known to inspire remineralization of hydroxyapatite tooth structure. Such compounds include: calcium, phosphorus and fluorine salts in forms such as dentifrices. Examples of such salts include, but are not limited to, fluoride or fluoride-containing compounds such as sodium fluoride, potassium fluoride, ammonium fluoride, sodium difluoride, potassium difluoride, ammonium difluoride, sodium silicofluoride, zinc fluoride, and stannous fluoride. Other dentifrices include, for example, ureases, acid phosphates, calcium carbonate, and magnesium carbonate. Examples of the acid phosphates which may be used include, for example, orthophosphoric acid, monosodium phosphate, monopotassium phosphate, disodium phosphate, dipotassium phosphate, monoamonium phosphate, hemisodium phosphate and sodium hexametaphosphate salts. The dentifrice is preferably included in the dental device in the amount sufficient to provide an effective, topical concentration at the tooth surface.

Other active components which may be incorporated within the interproximal device include hydrogen peroxide or other peroxide-producing components such as PVP $H_2O_2$ or Carbamide $H_2O_2$ Fluoride, tooth acidulating agents such as buffered or acidulated phosphofluoride, sodium monofluorophosphate, plaque control agents, tartar control agents, antibiotics to treat pyorrhea and gingivitis, teeth whitening and bleaching agents, pH buffering agents, antifungal agents, remineralizing agents, hemostatic agents, immunological agents and nonionic and cationic antibacterials such as benzothonium chloride, acetyl trimethyl ammonium bromide, sanguinaria, triclosan (nonionic), tetracycline, cetyl pyridinium chloride and benzythonium chloride.

Additional active components that can be included in the dental devices of the present invention include Vitamin A, surfactants and pharmacological agents such as anti-cancer agents, stimulants, bone growth agents, antigens, hormones, steroids, anti-inflammatory agents and analgesic agents.

In other embodiments, the dental device comprises a coagulant to inhibit any bleeding which may be produced by flossing. Preferably, the coagulant is mixed in the wax coating so as to directly contact the gum tissue. The coagulants may include vitamin K, calcium ions in the form of water-soluble calcium salts and blood factors that initiate the coagulation cascade. Alternatively, the coagulants may be solubilized in non-toxic solvents, such as ethanol, polyethylene terepthalate or diethyl ether.

Flavorants may be added to the dental devices of the present invention by techniques known in the art, such as adding the flavorant directly to the device after extrusion or by applying a flavored coating to the surface of the device, or by transferring volatile flavors to the device from a flavor reservoir. Known flavorants such as mint, cinnamon and bubble gum, which are commercially available through various suppliers including IFF Corporation, Dayton, N.J.; are suitable for use in the dental devices of the present invention. Other flavorants may also be added by the compression coating process described in the references cited.

Colorants may be added to the dental devices of the present invention to color the dental device in order to provide a visual stimulus to the consumer. Colorant can be added to the nylon or other pellets used to form the strand before extrusion begins. Any one of commercially available, FDA approved colorants for use with nylon resins may be used. Colors may correspond to the flavor of the dental device, e.g., red for cinnamon or green for mint. Further, multiple colors may be extruded simultaneously so that, for example, one side of the filament is red and other green. The device may further incorporate colorant agents or fluorescent dye to identify residual plaque deposits, such as, for example, FD&C Red 3 and FD&C Red 4.

Examples 1-13

The present invention is further described by additional enclosed samples of topical gels and dental tapes used to apply the vitamin D and UBIQUINOL supplement compositions of the invention to the oral mucosa and to interproximal surfaces, respectively.

Illustrative Example 1—Topical Oral Gel with Calcitriol

A Hobart N-50 mixer fitted with a 1 gallon stainless steel bowl and a nitrogen blanket was used to mix the following: PEG 400, 272 gm; Carbopol 974P, 16 gm; glycerin, 580.72 gm; xylitol powder, 48 gm; acesulfame K, 4.8 gm; titanium dioxide, 16 gm; zeodent 113, 80 gm; sipernat 22S, 120 gm; perlastin L, 8 gm; sucralose, 2.4 gm; and flavor, 21.6 gm were stirred for 5 minutes at room temperature. A separate 250 mL stainless vessel with overhead stirring under nitrogen blanket was heated to 80 degrees Centigrade with 183.2 gm poloxamer 407 and aqueous-free emulsion [poloxamer 407/polydimethylsiloxane (90:10)], 64 gm, and Calcitriol, 5 mg, was added to the 250 mL vessel. The contents were added to the one gallon vessel under nitrogen. After stirring for 2 minutes, the contents of the one gallon vessel were dispensed into 40 gm tubes for use. Application of 1 gram of gel to the oral mucosa delivers 50 IU of Calcitriol to oral mucosa.

Illustrative Example 2—Vitamin D PROPHY TAPE®

A 2 gallon stainless steel vessel was fitted with an overhead stirrer and placed on a hotplate. An aqueous-free emulsion [poloxamer 407/polydimethylsiloxane (12,500 CS) 90:10], 2062.4 gm was placed in the vessel and melted while stifling under a nitrogen blanket. The temperature rose to 90 degrees centigrade and the following ingredients were added: Pluracare L-1220, 120 gm; stearyl alcohol, 600 gm; microwax ML445, 280 gm and PEG 8000, 446 gm were added to the molten aqueous-free emulsion. A homogenizer was placed in the vessel and emulsification resulted from 10 minutes of action. The following ingredients were then added with stifling: silica, 160 gm; sodium saccharin, 96 gm; EDTA, 8 gm and flavor, 224 gm. Calcitriol, 100 mg, was added with stifling. The emulsified tape coating batter was then dispensed into the dental tape coating tank at 90 degrees Centigrade. Compression coating of ultra-high-molecular-weight polyethylene dental tape was completed to give a saliva soluble, coated, dental tape of 65 mg/yard. Use of one yard of the dental tape delivers 50 IU of Calcitriol to the oral mucosa.

Example 3

A 30 mL glass vial was fitted with a magnetic stirrer and a nitrogen flush while 5 gm of an aqueous-free emulsion of poloxamer 407/polydimethylsiloxane (2.5 million cs) was melted at 80-90 degrees C. Ascorbyl palmitate, 1 gm, was added with stifling. UBIQUINOL, 1 gm, was then added and finally, 8.37 gm of propylene glycol was added with continuing heating and stirring under nitrogen for 10-15 minutes. The vial was removed from stifling and heating and allowed to come to room temperature. The initial sample of UBIQUINOL had a slight yellow color due to exposure to air as a result to opening of a scaled package of UBIQUINOL. The experimental vial's relative color was compared to initial yellow level at first addition. After setting at room temperature for 24 hours, the color was evaluated. The sample color was medium yellow, indicating very little reduction of the CoQ10 contaminate by the ascorbyl palmitate.

A number of examples were prepared under the same conditions described for Example 4 with 5 gm of the aqueous-free emulsion (80% poloxamer 407 emulsified with polydimethylsiloxane, 2.5 million cs), ascorbyl palmitate at 1 gm and UBIQUINOL at 1 gm, as above:

Examples 3 to 11

| Example # | Composition | Other components added | Color Results |
| --- | --- | --- | --- |
| 3 | as executed in Example 3 | none | medium yellow |
| 4 | as executed in Example 3 | 2.39 gm glycerin added | medium yellow |
| 5 | as executed in Example 3 | 0.19 gm of methyl paraben | medium yellow |
| 6 | 5 gm of emulsion, 1 gm ascorbyl palmitate, 1 gm ubiquinol, | 1.85 gm of carboxymethyl-cellulose 9H4XF | medium yellow |
| 7 | as executed in Example 6 | 8.37 gm propylene glycol | all white |
| 8 | as executed in Example 6 | 1.0 gm carboxymethyl-cellulose 9H4XF | medium yellow |
| 9 | as executed in Example 7 | 0.5 gm carboxymethyl-cellulose 9H4XF | medium yellow |
| 10 | as executed in Example 6 | 1.0 gm carboxymethyl-cellulose 9H4XF | mottled yellow and white |
| 11 | as executed in Example 7 | 0.5 gm carboxymethyl-cellulose 9H4XF | mottled yellow and white |

These results indicate that the formulation comprising an aqueous-free emulsion, comprising UBIQUINOL, ascorbyl palmitate, propylene glycol and an amount of carboxymethylcellulose in a weight ratio from between about 1.5 and 2.5, imparts stability to UBIQUINOL, allowing topical UBIQUINOL compositions to adjunctively supplement UBIQUINOL levels.

Illustrative Example 12—Topical Oral Gel with Calcitriol and UBIQUINOL

A 500 mL stainless steel beaker was fitted with an overhead stirrer and a cover while flushing with nitrogen. Water, 135.834 gm, was added and moderate stifling began. The additional ingredients for this vessel were added: Sorbitol 70%, 102 gm; glycerin, 15 gm; potassium sorbate, 0.45 gm; sodium saccharin, 0.225 gm; sucralose, 0.6 gm, and flavors, 0.9525 gm, were added with moderate stifling at room temperature.

A 100 m beaker containing an aqueous-free emulsion [poloxamer 407/polydimethylsiloxane (2.5 million CS)] (90:10) at 9.54 gm, was heated to 95 degrees C. with magnetic stirring. Calcitriol, at 0.15 gm, and UBIQUINOL, at 0.15 gm, and ascorbyl palmitate, at 0.15 gm, was added to the beaker under a nitrogen blanket.

To a 50 mL beaker, with magnetic stifling and heating, was added propylene glycol, 30 gm and methyl paraben, 0.45 gm. When the temperature attained 50 degrees C., carboxymethylcellulose 9H4XF, 4.65 gm, was added slowly over 3 minutes. After 5 minutes of stifling, the contents were added slowly to the 100 mL beaker, containing the aqueous-free emulsion. After continued stirring and cooling to 40 degrees C., the contents were added to the stainless steel beaker slowly over 3 minutes. After an additional 20 minutes, the topical oral gel was packaged under a head of nitrogen for topical dispensing.

Illustrative Example 13—Vitamin D and UBIQUINOL SUPPLEMENT PROPHY TAPE® with SOFT ABRASIVES®

A 2 gallon stainless steel vessel was fitted with an overhead stirrer and placed on a hotplate. A nitrogen flush was added to the covered stirred vessel. An aqueous-free emulsion [poloxamer 407/polydimethylsiloxane (12,500 CS)] (90:10) 1964 gm, was placed in the vessel and melted while stifling. The temperature rose to 90 degrees C. and the following ingredients were added: Pluracare L-1220, 120 gm; stearyl alcohol, 600 gm; microwax ML445 and polyethylene glycol were added to the molten aqueous-free emulsion. A homogenizer was placed in the vessel and emulsification resulted from 10 minutes of action. The following ingredients were then added with stifling: Dicalcium phosphate dihydrate, dentifrice grade, 240 gm; propyl gallate, 4 gm; sodium saccharin, 72 gm; EDTA, 8 gm; and then the flavor, 248 gm, was added. Finally, calcitriol, 2 gm; UBIQUINOL, 12 gm; ascorbyl palmitate, 12 gm, was added to the emulsified coating. The emulsified tape coating batter was then dispensed into the tape coating tank. Compression coating of ultra-high-molecular-weight polyethylene dental tape was completed, followed by overcoating with bioglass SOFT ABRASIVE®.

The resulting PROPHY TAPE® with a saliva soluble, compression coating containing vitamin D and UBIQUINOL in an aqueous-free emulsion, overcoated with bioglass SOFT ABRASIVES®, was packaged in single-use pieces, collectively packaged in a flavor-sealed package and flavored by means of a flavor reservoir, containing 20 drops of a volatile flavor.

What is claimed is:

1. An aqueous free vitamin D and ubiquinol composition that forms, in situ, in the oral cavity, a saliva-soluble, mucoadhesive gel that is substantive to the oral mucosa for topically treating oral inflammation and oxidative stress, comprising:
    a saliva-soluble, aqueous-free, emulsion carrier;
    effective levels of vitamin D and ubiquinol that gradually dissolve from the mucoadhesive gel releasing said vitamin D and ubiquinol;
    a stabilizing composition for ubiquinol, which composition comprising ascorbyl palmitate, propylene glycol and carboxymethylcellulose; wherein the amount of carboxymethylcellulose is present in a percent ratio to the amount of ubiquinol between about 1.5 and about 2.5, and the weight ratio of the ascorbyl palmitate, propylene glycol, ubiquinol, and carboxymethylcellulose to aqueous-free emulsion, is between 1.5 and 2.5;
    a trans-oral mucosal absorption facilitator and spilanthes extract that are released onto said oral mucosa;
    wherein:
    (i) upon application to the oral mucosa, said composition forms in situ in the oral cavity a saliva-soluble, mucoadhesive gel that is substantive to said oral mucosa;
    (ii) upon continuous exposure of said saliva-soluble, mucoadhesive gel to saliva flow, said mucoadhesive gel gradually dissolves, effecting controlled release of said vitamin D and ubiquinol, said trans-oral mucosal absorption facilitator and said spilanthes extract onto said oral mucosa; and
    (iii) upon contacting said oral mucosa, said vitamin D and ubiquinol, spilanthes extract and trans-oral mucosal absorption facilitator passively diffuse through said oral mucosa:
        (a) regulating the in vivo availability and immune response of vitamin D and the oxidative stress associated with deficient ubiquinol levels;
        (b) restoring and maintaining adequate levels of circulating vitamin D and ubiquinol;
        (c) minimizing risk of hypercalcemia; and
        (d) treating oral inflammation and reducing oxidative stress.

2. The composition according to claim 1, wherein said saliva-soluble, aqueous-free emulsion comprises polydimethylsiloxane emulsified in a nonionic surfactant that is capable of forming a mucoadhesive gel in the presence of saliva.

3. The composition according to claim 1, wherein (i) said vitamin D is selected from the group consisting of:
    vitamin D compounds with hydroxyl groups at 1, 3 and 25 carbon positions,
    esters of 1α,25-dihydroxy vitamin D3,
    esters of 1,25-dihydroxy vitamin D3, 1,25 (OH)2D3 analogs of 1,25(OH)2D3,
calcitriol, 25(OH)D3, analogs of 25(OH)D3 and combinations thereof, and
(ii) said ubiquinol is represented by the structural formula:

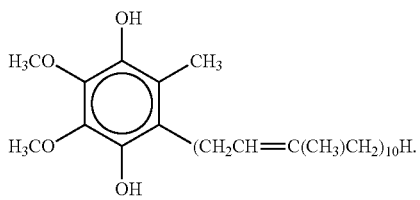

4. The composition according to claim 1, wherein said trans-oral mucosal absorption facilitator is selected from the group consisting of dexpanthenol, d-Limonene, poloxamer, polyethylene glycol (PEG), benzyl alcohol, carbopol, chitosan, N-trimethylchitosan, menthol and combinations thereof.

5. The composition according to claim 1, wherein the application means for said composition is selected from the group consisting of interproximal devices coated with said composition, oral gels, oral ointments, oral pastes, oral varnishes, oral sealants, oral rinses, oral liquids and combinations thereof.

6. A composition, according to claim 5, wherein said interproximal device application means is selected from the group consisting of compression coated dental tape, multifilament or monofilament dental floss or interproximal devices, coated one-handed: dental devices, dental picks, dental stimulators and combinations thereof.

7. The composition according to claim 2, wherein said polydimethylsiloxane is selected from the group consisting of polydimethylsiloxane at 1,500 cs, at 12,500 cs, at 100,000 cs, at 250,000 cs, at 500,000 cs, at 750,000 cs, at 1.5 million cs, at 2.2 million cs, at 2.5 million cs and combinations thereof.

8. The composition according to claim 2, wherein said nonionic surfactant is selected from the group consisting of poloxamer 237, poloxamer 338, poloxamer 407 and combinations thereof.

9. The composition according to claim 1, wherein said vitamin D enhances innate immunity by upregulating the antimicrobial peptide, cathelicidin; and said ubiquinol reduces oxidative stress by adjunctively increasing ubiquinol levels.

10. The composition, according to claim 1, wherein said vitamin D is 1α,25-dihydroxyvitamin D.

11. The composition according to claim 10, wherein said 1α,25-dihydroxyvitamin D's effects on the immune system include:
Modulating T-cell receptor,
decreasing TH1/TH1/CD4 and T cells and cytokines,
increasing regulatory T cells,
down regulating T cell-driven production, and
inhibiting dendritic cell differentiation.

12. The composition of claim 1 wherein the following components are in a ratio of: 5 g of aqueous free emulsion to 1 g of ascorbyl palmitate to 1 g of ubiquinol to 1.85 g of carboxy-methyl-cellulose, and to 8.37 g of propylene glycol.

13. An aqueous free therapeutic mixture for relieving oral discomfort comprising an aqueous-free, oxygen-free emulsion of polydimethylsiloxane as the discontinuous phase and poloxamer as the continuous phase wherein the aqueous-free, oxygen free emulsion comprises polydimethylsiloxane selected from the group consisting of polydimethylsiloxane at 1,500 cs, 12,500 cs, 100,000 cs, 250,000 cs, 750,000 cs 1.5 million cs 2.2 millions cs, 2.5 million cs, and combinations thereof, and wherein the nonionic surfactant is selected from the group consisting of poloxamer 237, poloxamer 338, poloxamer 407, and combinations thereof, and combinations thereof; and said emulsion containing ubiquinol, ascorbyl palmitate, Vitamin D, spilanthes extract, a calcium salt, and monosodium phosphate; and a stabilizing composition for ubiquinol, which composition comprising ascorbyl palmitate, propylene glycol and carboxymethylcellulose; wherein the amount of carboxymethylcellulose is present in a percent ratio to the amount of ubiquinol between about 1.5 and about 2.5, and the weight ratio of the ascorbyl palmitate, propylene glycol, ubiquinol, and carboxymethylcellulose to aqueous-free emulsion, is between 1.5 and 2.5;
wherein upon administration of said aqueous-free, oxygen free emulsion to oral mucosa, said emulsion forming a mucoadhesive gel coating that slowly dissolves in the oral mucosa, while simultaneously releasing the following ingredients:
(a) ubiquinol, substantially free from ubiquinone;
(b) an effective amount of Vitamin D;
(c) spilanthes extract, at a level sufficient to effect trans-oral mucosal absorption of said ubiquinol and said Vitamin D, prior to saliva solubilization of said mucoadhesive gel coating; and
(d) a calcium salt and monosodium phosphate, released as unreacted salts suitable for combining with residual fluoride present in the oral mucosa.

14. The therapeutic mixture of claim 13 wherein the vitamin D supplement in the mixture is selected from the group consisting of:
Vitamin D, Vitamin D compounds with hydroxyl groups at 1, 3 and 25 carbon positions, esters of 1α,25-dihydroxy vitamin D3, esters of 1,25-dihydroxy vitamin D3,
1,25 (OH)2D3 analogs of 1,25(OH)2D3, Calcitriol, 25(OH)D3, analogs of 25(OH)D3 and combinations thereof; and, wherein
said ubiquinol supplement is represented by the structural formula:

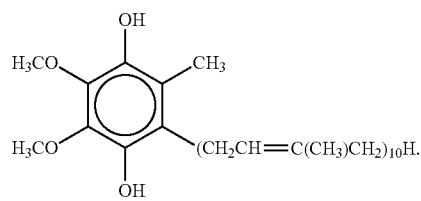

15. A method for treating oral inflammation and oxidative stress, comprising topically administering a vitamin D and ubiquinol supplement composition to the oral mucosa comprising:
a saliva soluble, aqueous-free emulsion carrier, wherein said saliva soluble, aqueous-free emulsion is comprised of polydimethylsiloxane emulsified in a nonionic surfactant that is capable of forming a mucoadhesive gel in the presence of saliva;
an effective level of vitamin D and ubiquinol supplements;
a stabilizing composition for ubiquinol, which composition comprising ascorbyl palmitate, propylene glycol and carboxymethylcellulose; wherein the amount of carboxymethylcellulose is present in a percent ratio to the amount of ubiquinol between about 1.5 and about 2.5, and the weight ratio of the ascorbyl palmitate, propylene glycol, ubiquinol, and carboxymethylcellulose to aqueous-free emulsion, is between 1.5 and 2.5;

a trans-oral mucosal, absorption facilitator; and spilanthes extract; and wherein said composition is substantially aqueous free; wherein: upon application to the oral mucosa, said composition forms a saliva soluble, mucoadhesive gel, substantive to said oral mucosa;

upon continuous exposure of said saliva soluble, mucoadhesive gel to saliva flow, said mucoadhesive gel gradually dissolves effecting controlled release of said vitamin D and ubiquinol supplement mixture, a stabilizing composition for ubiquinol, said trans-oral mucosal, absorption facilitator and spilanthes extract onto said oral mucosa;

and upon contacting said oral mucosa, said vitamin D and ubiquinol supplement mixture, Spilanthes extract and trans-oral mucosal, absorption facilitator passively diffuse through said oral mucosa:
  (a) regulating the in vivo availability and immune response of vitamin D and ubiquinol;
  (b) maintaining adequate levels of circulating vitamin D and ubiquinol;
  (c) minimizing risk of hypercalcemia; and
  (d) treating oral inflammation and reducing oxidative stress.

16. A method, according to claim 15, wherein said vitamin D supplement in the mixture is selected from the group consisting of:

Vitamin D,
Vitamin D compounds with hydroxyl groups at 1, 3 and 25 carbon positions, esters of 1α,25-dihydroxy vitamin D3,
esters of 1,25-dihydroxy vitamin D3,
1,25 (OH)2D3 analogs of 1,25(OH)2D3,
Calcitriol, 25(OH)D3, analogs of 25(OH)D3 and combinations thereof; and said ubiquinol supplement is represented by the structural formula:

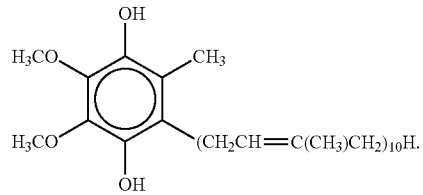

17. A method, according to claim 15, wherein said trans-oral mucosal, absorption facilitators are selected from the group consisting of: dexpanthenol, d-Limonene, poloxamer, PEG, benzyl alcohol, carbopol, chitosan, N-trimethylchitosan, menthol and combinations thereof.

18. A method, according to claim 15, wherein application means for said topical vitamin D and ubiquinol, oral supplement composition is selected from the group consisting of interproximal devices coated with said composition, oral gels, oral ointments, oral pastes, oral varnishes, oral sealants, oral rinses, oral liquids and combinations thereof.

19. A method for treating oral inflammation and oxidative stress, comprising topically administering vitamin D and ubiquinol supplement compositions, according to claim 15, wherein said composition is applied repetitively throughout the day with a vitamin D and ubiquinol supplement gel in combination with daily topical administration with a dental device coated with said composition.

* * * * *